United States Patent
Ran et al.

(10) Patent No.: US 9,757,477 B2
(45) Date of Patent: Sep. 12, 2017

(54) IMAGING BROWN ADIPOSE TISSUE WITH CURCUMIN DERIVATIVES

(71) Applicant: The General Hospital Corporation, Boston, MA (US)

(72) Inventors: Chongzhao Ran, Winchester, MA (US); Anna Moore, Stoneham, MA (US); Anna-Liisa Brownell, Salem, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/916,779

(22) PCT Filed: Sep. 4, 2014

(86) PCT No.: PCT/US2014/054012
§ 371 (c)(1),
(2) Date: Mar. 4, 2016

(87) PCT Pub. No.: WO2015/034996
PCT Pub. Date: Mar. 12, 2015

(65) Prior Publication Data
US 2016/0193363 A1 Jul. 7, 2016

Related U.S. Application Data

(60) Provisional application No. 61/874,755, filed on Sep. 6, 2013.

(51) Int. Cl.
| | |
|---|---|
| *A61K 49/06* | (2006.01) |
| *A61K 51/04* | (2006.01) |
| *A61K 49/00* | (2006.01) |
| *C07D 401/06* | (2006.01) |
| *C07D 403/06* | (2006.01) |
| *C07D 471/04* | (2006.01) |
| *A61K 49/22* | (2006.01) |

(52) U.S. Cl.
CPC ...... *A61K 49/0002* (2013.01); *A61K 49/0017* (2013.01); *A61K 49/06* (2013.01); *A61K 49/22* (2013.01); *A61K 51/04* (2013.01); *C07D 401/06* (2013.01); *C07D 403/06* (2013.01); *C07D 471/04* (2013.01)

(58) Field of Classification Search
CPC ........ A61K 49/00; A61K 49/06; A61K 49/22; A61K 51/04
See application file for complete search history.

(56) References Cited

U.S. PATENT DOCUMENTS

| | | | |
|---|---|---|---|
| 4,522,811 A | 6/1985 | Eppstein et al. | |
| 6,468,798 B1 | 10/2002 | Debs et al. | |
| 6,471,996 B1 | 10/2002 | Sokoll et al. | |
| 6,472,375 B1 | 10/2002 | Hoon et al. | |
| 6,503,713 B1 | 1/2003 | Rana | |
| 6,881,584 B1 | 4/2005 | Lenhard et al. | |
| 6,983,753 B1 | 1/2006 | Lenhard et al. | |
| 7,277,744 B2 | 10/2007 | Schaefer et al. | |
| 2007/0060644 A1 | 3/2007 | Vander et al. | |
| 2008/0033055 A1 | 2/2008 | Miller et al. | |
| 2008/0146660 A1 | 6/2008 | Lee et al. | |
| 2008/0161391 A1 | 7/2008 | Lee et al. | |
| 2010/0216859 A1 | 8/2010 | Chen | |
| 2011/0208064 A1* | 8/2011 | Chongzhao | ........ A61K 49/0021 600/476 |
| 2014/0275969 A1* | 9/2014 | Lau | ........ A61M 5/007 600/412 |
| 2015/0087937 A1 | 3/2015 | Chongzhao et al. | |
| 2015/0158841 A1 | 6/2015 | Ran et al. | |

FOREIGN PATENT DOCUMENTS

| | | |
|---|---|---|
| CN | 102603782 | 7/2012 |
| WO | WO 2010/074971 | 1/2010 |
| WO | WO2010/017094 | 2/2010 |
| WO | WO 2010/068935 | 6/2010 |
| WO | WO 2010/132815 | 11/2010 |
| WO | WO 2011/014648 | 2/2011 |

OTHER PUBLICATIONS

Y Iris Chen et al. Anatomical and Functional Assessment of Brown Adipose Tissue by Magnetic Resonance Imaging, Obesity, 20, 1519-1526, 2012.*
International Search Report and Written Opinion dated Nov. 2014 in International Application No. PCT/US2014/054012, 15 pgs.
Aleo et al., "Mechanism and Implications of Brown Adipose Tissue Proliferation in Rats and Monkeys Treated with the Thiazolidinedione Darglitazone, a Potent Peroxisome Proliferator-Activated Receptor-γ Agonist," The Journal of Pharmacology and Experimental Therapeutics, 2003, 305:1173-1182.
Baranova et al., "CD36 is a Novel Serum Amyloid A (SAA) Receptor Mediating SAA Binding and SAA-induced Signaling in Human and Rodent Cells," J Biol Chem, Mar. 2010, 285(11):8492-8506.
Bartelt et al., "Brown adipose tissue activity controls triglyceride clearance," Nature Medicine, Feb. 2011, 17(2): 200-205.
Basu, "Functional imaging of brown adipose tissue with PET: can this provide new insights into the pathophysiology of obesity and thereby direct antiobesity strategies?," Nuclear Medicine Communications, 2008, 29(11): 931-933.
Berge et al., "Pharmaceutical Salts," J Pharmaceutical Sci, 66(1):1-19 (1977).
Boss and Farmer, "Recruitment of brown adipose tissue as a therapy for obesity-associated diseases," Frontiers in Endocrinology, Feb. 2012, 3: 118-123.
Bostrom et al., "A PGC1α-dependent myokine that drives browning of white fat and thermogenesis," Nature, 481: 463-468.
Burcelin et al., "Changes in uncoupling protein and GLUT4 glucose transporter expressions in interscapular brown adipose tissue of diabetic rats: relative roles of hyperglycaemia and hypoinsulinaemia," The Biochemical Journal, 1993, 291: 109-113.
Cannon and Nedergaard, "Brown adipose tissue: function and physiological significance," Physiological Reviews, Jan. 2004, 84: 277-359.
Chen et al., "Anatomical and Functional Assessment of Brown Adipose Tissue by Magnetic Resonance Imaging. Obesity," Jul. 2012, 20(7): 1519-1526.

(Continued)

*Primary Examiner* — Michael G Hartley
*Assistant Examiner* — Jagadishwar Samala
(74) *Attorney, Agent, or Firm* — Fish & Richardson P.C.

(57) ABSTRACT

Methods and compositions for imaging Brown adipose tissue (BAT) in living mammals, e.g., humans.

20 Claims, 17 Drawing Sheets

(56) References Cited

OTHER PUBLICATIONS

Coburn et al., "Role of CD36 in membrane transport and utilization of long-chain fatty acids by different tissues," J Mol Neurosci., 2001, 16(2-3):117-121.
Cypess et al., "Identification and importance of brown adipose tissue in adult humans," The New England Journal of Medicine, Apr. 2009,360: 1509-1517.
Czarnik, "Encoding methods for combinatorial chemistry," Curr. Opin. Chem. Bio., Jun. 1997, 1:60-6.
Demers et al., "Identification of the growth hormone-releasing peptide binding site in CD36: a photoaffinity cross-linking study," Biochem. J., 2004, 382:417-424.
Farmer, "Molecular determinants of brown adipocyte formation and Function," Genes & Development, 2008, 22: 1269-1275.
Garcia-Alloza et al., "Curcumin labels amyloid pathology in vivo, disrupts existing plaques, and partially restores distorted neurites in an Alzheimer mouse model," J. Neurochem., Aug. 2007, 102: 1095-1104.
Greenwalt et al., "Heart CD36 Expression is Increased in Murine Models of Diabetes and in Mice Fed a High Fat Diet," J Clin Invest., 1995, 96(3):1382-1388.
Gunawardana and Piston, "Reversal of type 1 diabetes in mice by brown adipose tissue transplant," Diabetes, Mar. 2012, 61: 674-682.
Hamajima et al., "Intranasal administration of HIV-DNA vaccine formulated with a polymer, carboxymethylcellulose, augments mucosal antibody production and cell-mediated immune response," Clin Immunol Immunopathol. Aug. 1998;88(2):205-10.
Harmon and Abumrad, "Binding of sulfosuccinimidyl fatty acids to adipocyte membrane proteins: Isolation and ammo-terminal sequence of an 88-kD protein implicated in transport of long-chain fatty acids," J Membr Biol., Apr. 1993, 133(1):43-9.
Haucke et al., "The effect of internal rotation on absorption and fluorescence of dye molecules," Journal of Molecular Structure, Mar. 1990, 219: 411-416.
Herrero et al., "Inflammation and adipose tissue macrophages in lipodystrophic mice," PNAS, Jan. 2010, 107: 240-245.
Himms-Hagen et al., "Multilocular fat cells in WAT of CL-316243-treated rats derive directly from white adipocytes," American Journal of Physiology Cell Physiology, 2000, 279: C670-681.
Hu et al., "Identification of brown adipose tissue in mice with fat-water IDEAL-MRI," Journal of Magnetic Resonance Imaging, 2010, 31: 1195-1202.
International Preliminary Report on Patentability in International Application No. PCT/US2013/053833, dated Feb. 10, 2015, 7 pages.
International Preliminary Report on Patentability in International Application No. PCT/US2014/054012, dated Mar. 8, 2016, 9 pages.
International Search Report and Written Opinion dated Dec. 5, 2013 in international application No. PCT?US2013/053833, 10 pages.
Jamal and Saggerson, "Changes in brown-adipose-tissue mitochondrial processes in streptozotocin-diabetes," The Biochemical Journal, 1988, 252: 293-296.
Kajimura et al., "Regulation of the brown and white fat gene programs through a PRDM16/CtBP transcriptional complex," Genes & Development, 2008, 22: 1397-1409.
Kaplan et al., "Membrane proteins and urea and acetamide transport in the human erythrocyte," J. Membr Biol., Dec. 1975, 20:181-190.
Khanna and Branca, "Detecting brown adipose tissue activity with BOLD MRI in mice," Magnetic Resonance in Medicine, Oct. 2012, 68: 1286-1290.
Kim et al, "Effect of adipocyte beta3-adrenergic receptor activation on the type 2 diabetic MKR mice," American Journal of Physiology Endocrinology and Metabolism, Jun. 2006, 290: E1227-1236.
Madar et al., "18F-fluorobenzyl triphenyl phosphonium: a noninvasive sensor of brown adipose tissue thermogenesis," Journal of Nuclear Medicine, May 2011, 52(5): 808-814.
Massoud et al., "Molecular imaging in living subjects: seeing fundamental biological processes in a new light," Genes and Development, 2003, 17: 545-580.

Mattson, "Does brown fat protect against diseases of aging?," Ageing Research Reviews, Jan. 2010, 9: 69-76.
Nagajyothi et al., "Response of adipose tissue to early infection with Trypanosoma cruzi (Brazil strain)," The Journal of Infectious Diseases, 2012, 205: 830-840.
Nedergaard et al, "Unexpected evidence for active brown adipose tissue in adult humans," American Journal of Physiology Endocrinology and Metabolism, 2007, 293: E444-452.
Ocloo et al, "Cold-induced alterations of phospholipid fatty acyl composition in brown adipose tissue mitochondria are independent of uncoupling protein-1," American Journal of Physiology Regulatory, Integrative and Comparative Physiology, Sep. 2007, 293(3): R1086-1093.
Ouellet et al., "Brown adipose tissue oxidative metabolism contributes to energy expenditure during acute cold exposure in humans," The Journal of Clinical Investigation, 2012, 122: 545-552.
Pfannenberg et al., "Impact of age on the relationships of brown adipose tissue with sex and adiposity in humans," Diabetes, Jul. 2010, 59: 1789-1793.
Popic et al., "An Improved Synthesis of 2-diazo-1,3-diketones," Synthesis, 1991, 3:195-8.
Qiang et al., "Brown Remodeling of White Adipose Tissue by SirT1-Dependent Deacetylation of Pparγ," Cell, Aug. 2012, 150: 620-632.
Ran and Moore, "Spectral Unmixing Imaging of Wavelength-Responsive Fluorescent Probes: An Application for the Real-Time Report of Amyloid Beta Species in Alzheimer's Disease," Mol. Imaging Biol., Jun. 2012, 14(3): 293-300.
Ran et al., "Design, synthesis, and testing of difluoroboron derivatized curcumins as near infrared probes for in vivo detection of amyloid-β deposits," Journal of American Chemical Society, Oct. 2009, 131(42): 15257-15261.
Ran et al., "Non-conjugated small molecule FRET for differentiating monomers from higher molecular weight amyloid beta species," PLoS One. Apr. 29, 2011;6(4):e19362, 6 pages.
Ravin, "Preformulation," Remington's Pharmaceutical Sciences, 17th ed., Mack Publishing Company, Easton, Pa., 1985, pp. 1409-1418.
Richard and Picard, "Brown fat biology and thermogenesis," Frontiers in Bioscience, Jan. 2011, 16: 1233-1260.
Ryu et al., "Curcumin and Dehydrozingerone Derivatives: Synthesis, Radiolabeling, and Evaluation for β-Amyloid Plaque Imaging." J. Med. Chem, 2006, 49: 6111-6119.
Sandoval et al., "Fatty acid transport and activation and the expression patterns of genes involved in fatty acid trafficking," Arch. Biochem. Biophysics, Sep. 2008, 477:363-371.
Schulz et al., "Brown-fat paucity due to impaired BMP signalling induces compensatory browning of white fat," Nature, Mar. 2013, 495: 379-383.
Seydoux et al., "Brown adipose tissue metabolism in streptozotocin-diabetic rats," Endocrinology, 1983, 113: 604-610.
Shoup et al., "F-18 labeled bis-dialkylamino-curcuminoid as a potential amyloid-beta imaging agent," J Nucl Med, May 2011; 52:1538.
Tatsumi et al., "Intense (18)F-FDG uptake in brown fat can be reduced pharmacologically," Journal of Nuclear Medicine, Jul. 2004, 45(7): 1189-1193.
Tran and Kahn, "Transplantation of adipose tissue and stem cells: role in metabolism and disease," Nature Reviews Endocrinology, Apr. 2010, 6: 195-213.
Tseng et al., "New role of bone morphogenetic protein 7 in brown adipogenesis and energy expenditure," Nature, Aug. 2008, 454: 1000-1004.
Ulrich et al., "The Chemistry of Fluorescent Bodipy Dyes: Versatility Unsurpassed," Agnew Chem. Int. Ed., Feb. 2008, 47: 1184-1201.
Van Marken Lichtenbelt et al., "Cold-activated brown adipose tissue in healthy men," The New England Journal of Medicine, Apr. 2009, 360: 1500-1508.
Weissleder, "A clearer vision for in vivo imaging," Nature Biotechnology, Apr. 2001, 19:316-317.
Williams and Fisher, "Globular warming: how fat gets to the furnace," Nat. Med., Feb. 2011, 17: 157-159.

(56) References Cited

OTHER PUBLICATIONS

Wilson-Fritch et al., "Mitochondrial remodeling in adipose tissue associated with obesity and treatment with rosiglitazone," The Journal of Clinical Investigation, Nov. 2004,114(9): 1281-1289.

Wu et al., "Brown adipose tissue can be activated or inhibited within an hour before 18F-FDG injection: a preliminary study with microPET," Journal of Biomedicine & Biotechnology, 2011, 2011: 159834.

Xu et al., "Exercise ameliorates high-fat diet-induced metabolic and vascular dysfunction, and increases adipocyte progenitor cell population in brown adipose tissue," American Journal of Physiology Regulatory, Integrative and Comparative Physiology, 2011, 300: R1115-1125.

Yang et al., "Curcumin Inhibits Formation of Amyloid Oligomers and Fibrils, Binds Plaques, and Reduces Amyloid in Vivo," J. Biol. Chem., 2005, 280: 5892-5901.

Yoneshiro et al., "Age-related decrease in cold-activated brown adipose tissue and accumulation of body fat in healthy humans," Obesity, Sep. 2011, 19: 1755-1760.

Zhang et al, "Cross talk between insulin and bone morphogenetic protein signaling systems in brown adipogenesis," Molecular and Cellular Biology, Sep. 2010, 30: 4224-4233.

Zhang et al., "Multi-Emissive Difluoroboron Dibenzoylmethane Polylactide Exhibiting Intense Fluorescence and Oxygen-Sensitive Room-Temperature Phosphorescence," J. Am. Chem. Soc., 2007, 129: 8942-8943.

Zhang, "In Vivo Optical Imaging of Interscapular Brown Adipose Tissue with 18F-FDG via Cerenkov Luminescence Imaging," Plos One, Apr. 2013, 8(4): e62007.

Zhou et al., "CD36 level and trafficking are determinants of lipolysis in adipocytes," FASEB J., Nov. 2012, 26(11):4733-42.

"FDA-approved radiopharmaceuticals," Cardinal Health, Jun. 2016, pp. 1-6.

Office Action in U.S. Appl. No. 14/419,985, dated Nov. 18, 2016, 9 pages.

Office Action in U.S. Appl. No. 14/515,665, dated Feb. 24, 2017, 16 pages.

Office Action in U.S. Appl. No. 14/515,665, dated Jul. 26, 2016, 16 pages.

Wang et al., "In Vivo Imaging of Histone Deacetylases (HDACs) in the Central Nervous System and Major Peripheral Organs," J Med Chem, 2014, 57: 7999-8009.

* cited by examiner

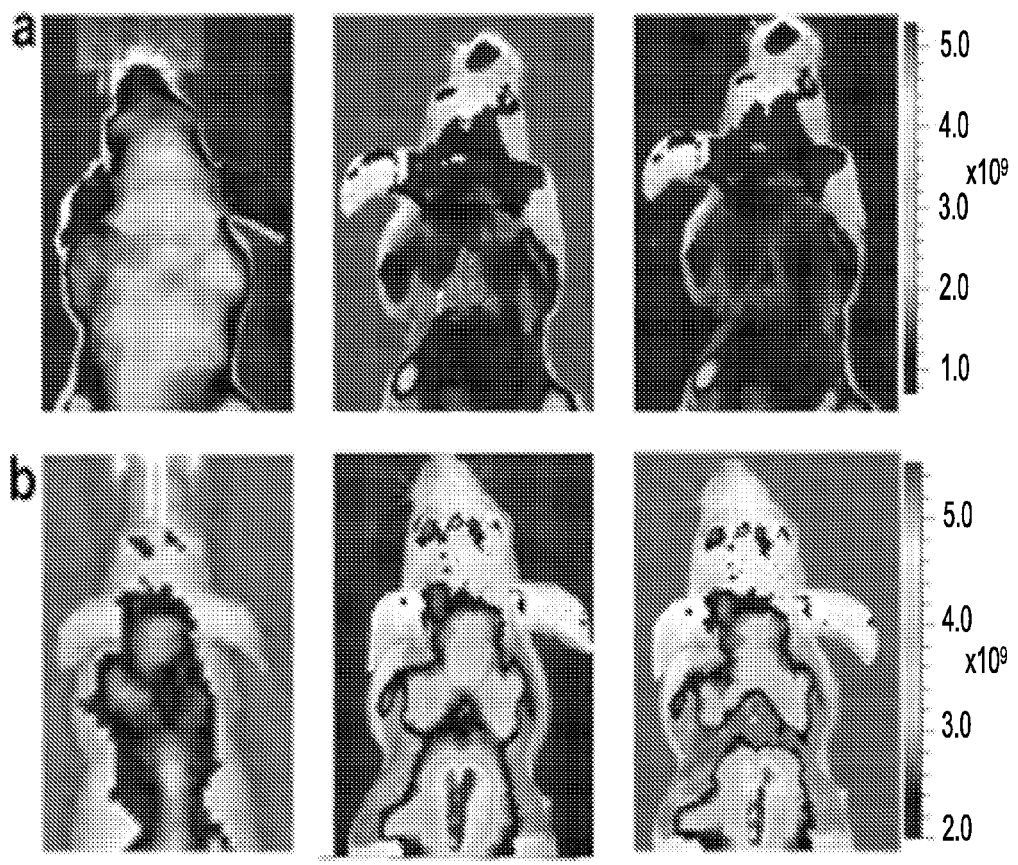
FIGs. 7A-B

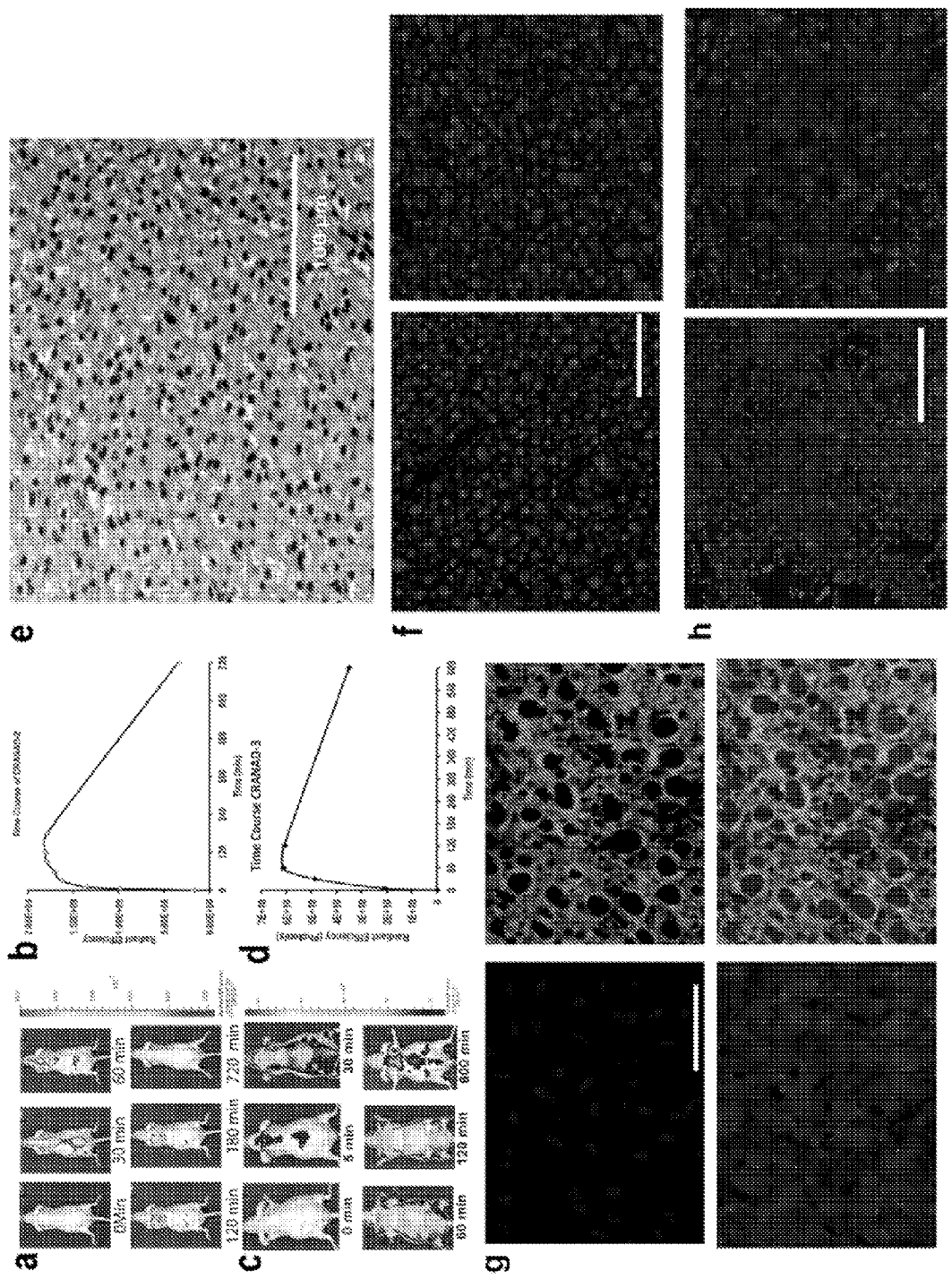
FIGs. 8A-H

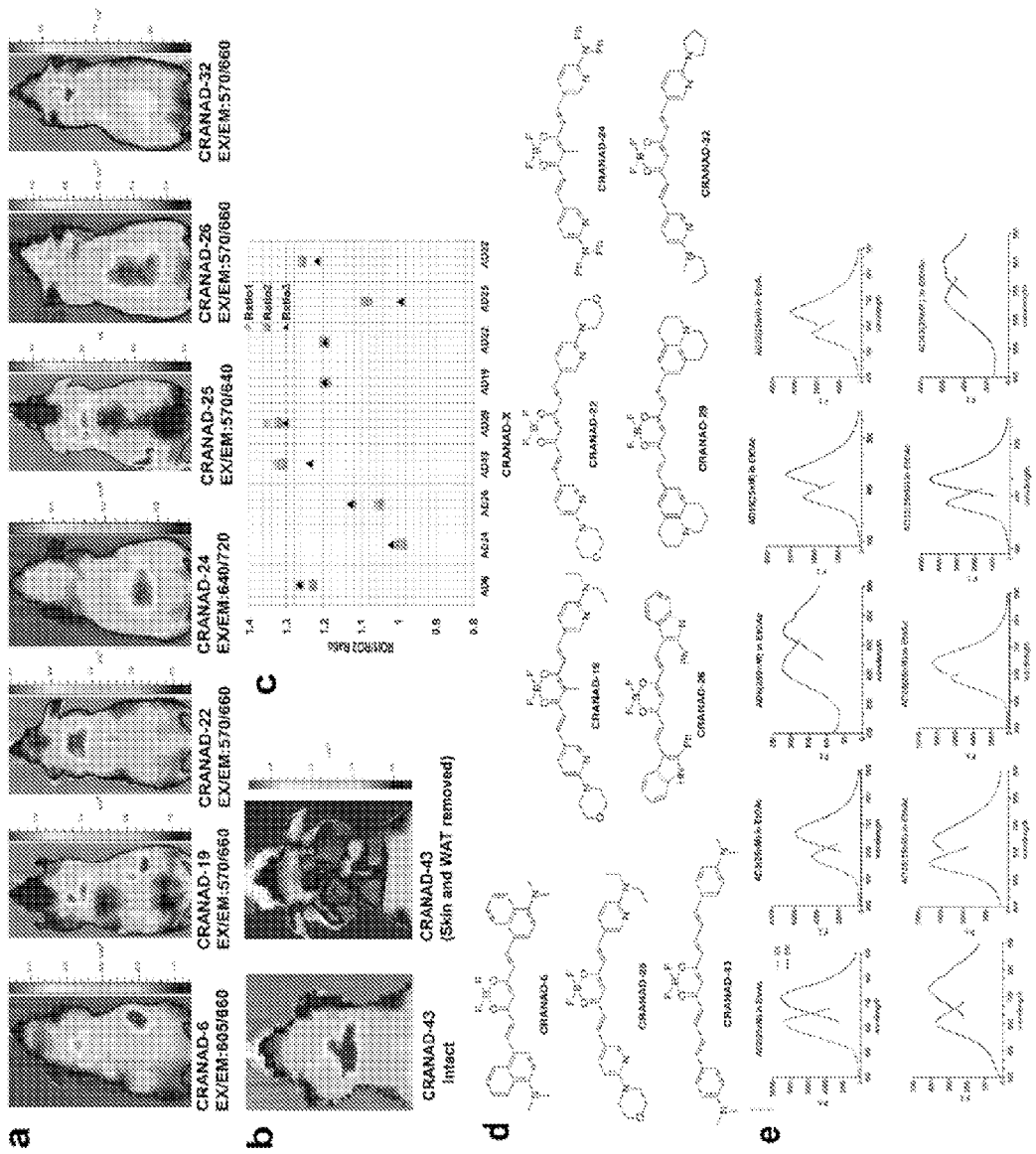
FIGs. 9A-E

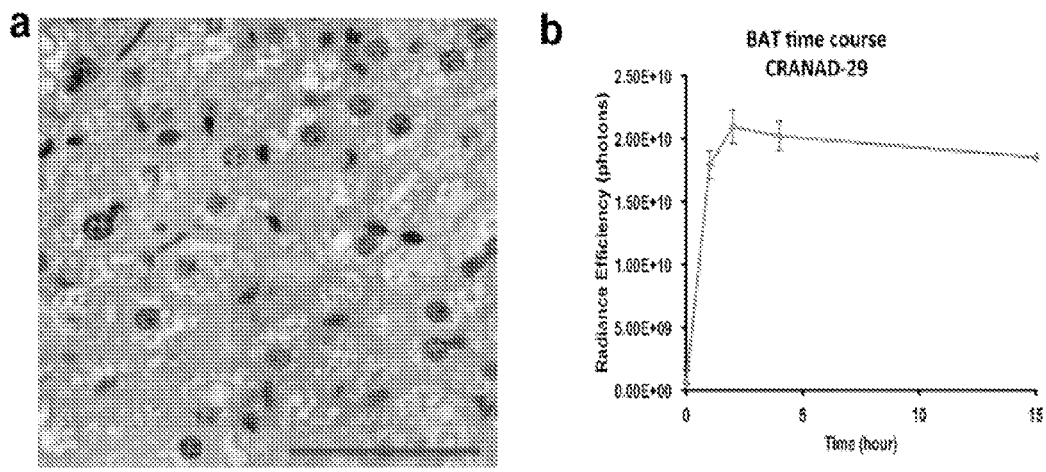
FIGs. 10A-B
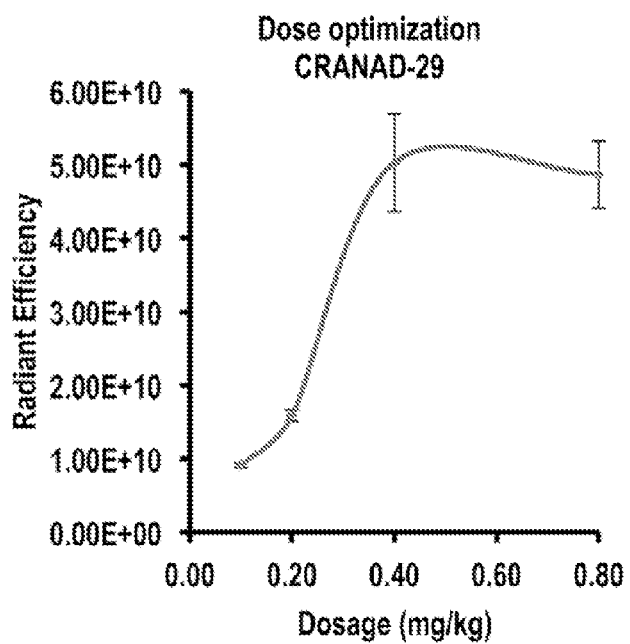
FIG. 11

FIGs. 12A-C

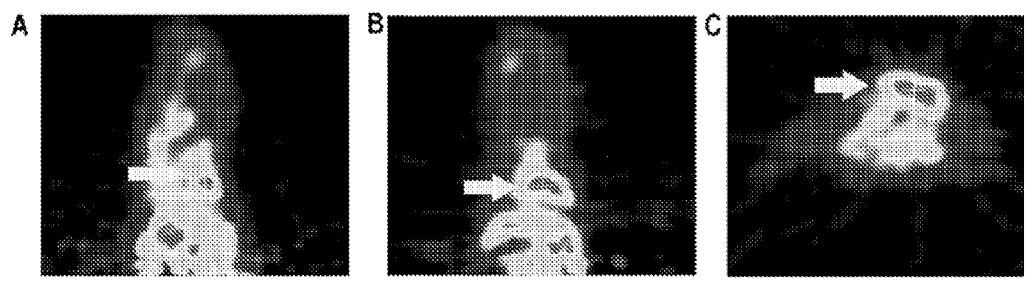
FIGs. 14A-C
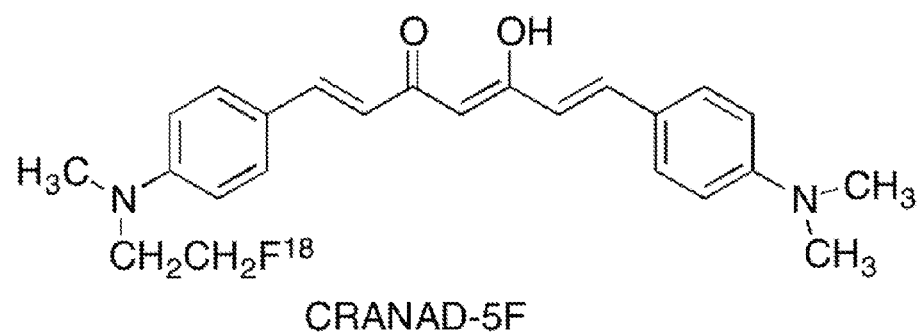
FIG. 14D

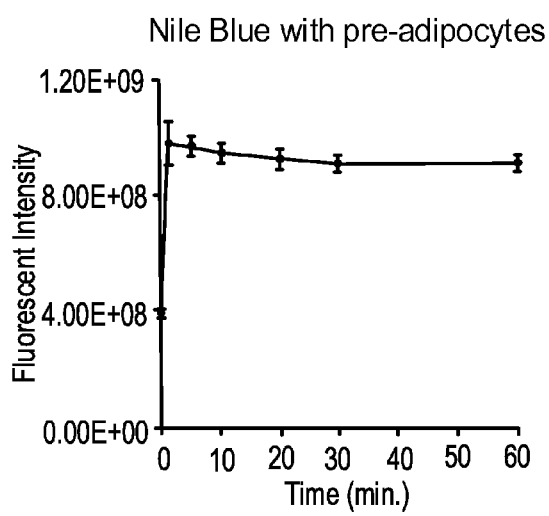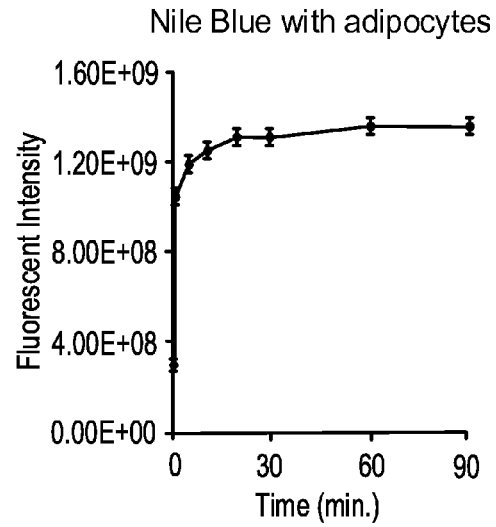
FIG. 16A
FIG. 16B
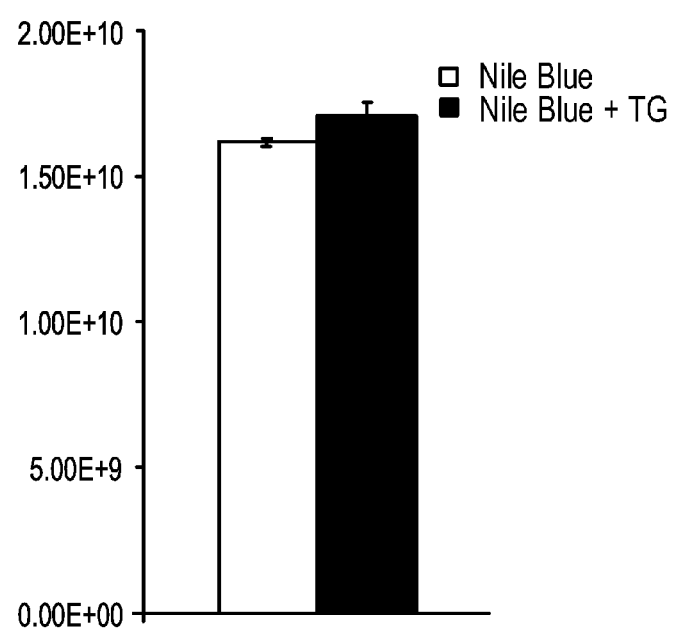
FIG. 16C

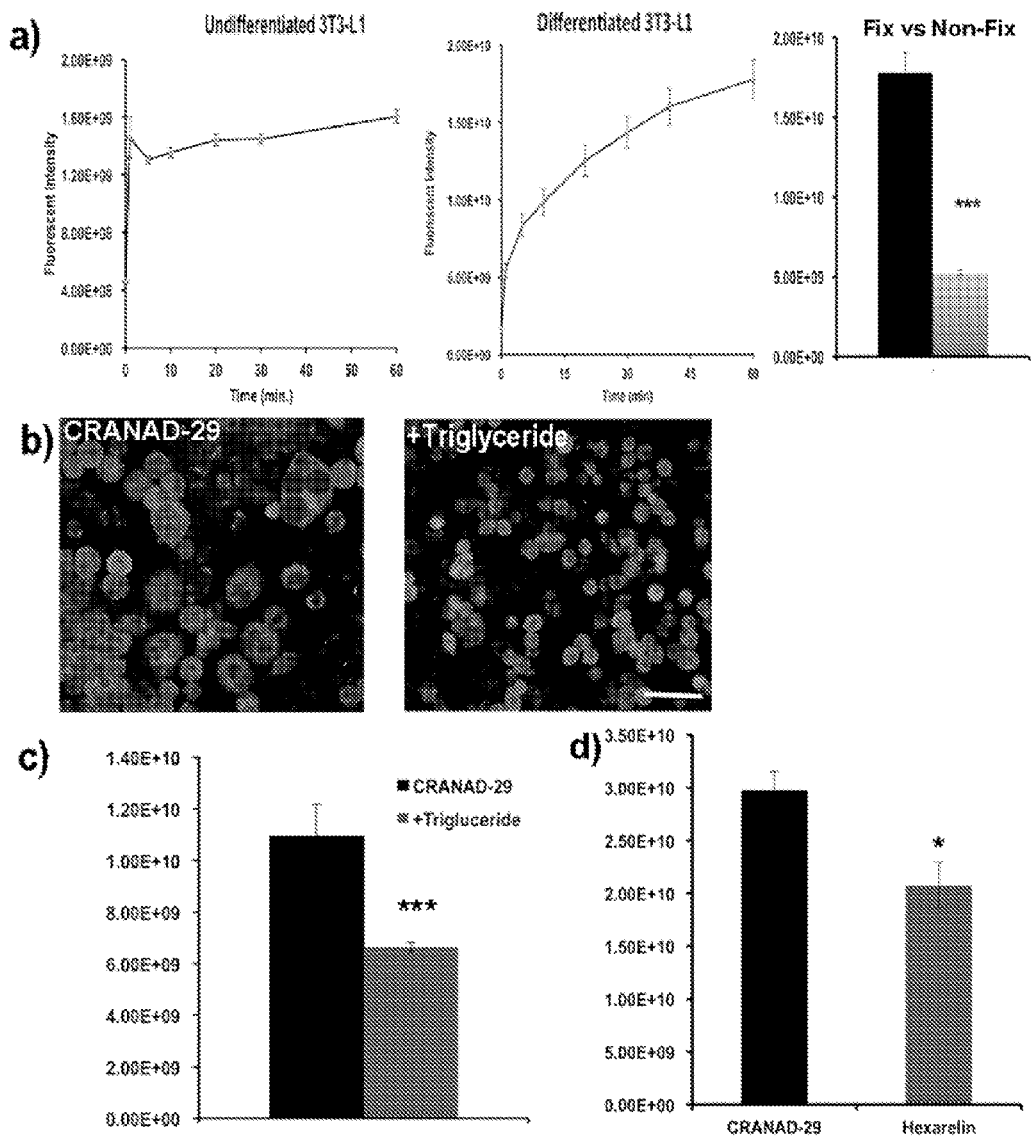
FIGs. 17A-D

IMAGING BROWN ADIPOSE TISSUE WITH CURCUMIN DERIVATIVES

CLAIM OF PRIORITY

This application is a U.S. National Phase Application under 35 U.S.C. §371 of International Patent Application No. PCT/US2014/054012, filed on Sep. 4, 2014, which claims the benefit of U.S. patent application Ser. No. 61/874,755, filed on Sep. 6, 2013. The entire contents of the foregoing are hereby incorporated by reference.

TECHNICAL FIELD

Methods and compositions for imaging Brown adipose tissue (BAT) in living mammals, e.g., humans.

BACKGROUND

Brown adipose tissue (BAT), widely known as 'good fat', has recently emerged as an important target for diabetes, obesity and other diseases. Imaging probe that could consistently monitor BAT mass and browning of white adipose tissue (WAT) is highly desirable.

SUMMARY

The present invention is based, at least in part, on the discovery that certain curcumin analogs can be used to non-invasively image BAT in vivo. Thus, described herein are methods for imaging BAT levels (mass) and activity using these analogs; methods for monitoring BAT levels and activity over time and in response to various treatments; and methods for selecting and stratifying subjects in clinical trials.

Thus, in one aspect the invention provides methods for imaging brown adipose tissue (BAT) in a mammal. The methods include administering to the mammal a BAT imaging agent as described herein, and detecting the imaging agent in the mammal, thereby imaging BAT in the mammal.

In another aspect, the invention provides methods for detecting brown adipose tissue (BAT) levels or activity in a mammal. The methods include administering to the mammal a BAT imaging agent as described herein; detecting the imaging agent in the mammal, to obtain an image of BAT in the mammal; and processing the image to provide a measure of BAT levels or activity in the mammal.

In another aspect, the invention provides methods for detecting an effect of a test compound on brown adipose tissue (BAT) levels or activity in a mammal. The methods include administering a test compound to the mammal; administering to the mammal a BAT imaging agent as described herein; and detecting the imaging agent in the mammal, to obtain an image of BAT in the mammal; processing the image to provide a measure of BAT levels or activity in the mammal after administration of the test compound; comparing the measure of BAT levels or activity in the mammal after administration of the test compound to a reference measure of BAT levels or activity (e.g., a reference measure of BAT levels or activity in the mammal before administration of the test compound, or a reference measure that represents BAT levels or activity in a control subject in the absence of the test compound), to detect an increase, decrease, or no change in BAT levels or activity in the mammal; thereby determining the effect of the test compound on BAT levels or activity in the mammal.

In some embodiments, the methods include selecting a test compound that increases BAT levels or activity in the mammal as a candidate compound for the treatment of obesity or a metabolic disorder, e.g., metabolic syndrome or diabetes.

In some embodiments, detecting the imaging agent in the mammal comprises setting a region of interest (ROI); and obtaining an image of the region of interest in the mammal. In some embodiments, the ROI includes an area comprising white adipose tissue (WAT) in the subject, and an increase in BAT levels or activity in the ROI indicates that the test compound induces or enhances browning of white fat.

In another aspect, the invention provides methods for selecting a mammalian subject for participation in, or stratifying subjects within, a clinical trial, based on brown adipose tissue (BAT) levels or activity in the subject, the method comprising: administering to the subject a BAT imaging agent as described herein; detecting the imaging agent in the subject, to obtain an image of BAT in the subject; processing the image to determine a measure of BAT levels or activity in the subject; and selecting, rejecting, or stratifying the subject based on BAT levels or activity in the subject.

In another aspect, the invention provides methods for monitoring efficacy of a therapy to increases brown adipose tissue (BAT) levels or activity in a mammal, the method comprising administering to the mammal a BAT imaging agent as described herein; detecting the imaging agent in the mammal, to obtain an image of BAT in the mammal; processing the image to provide a first measure of BAT levels or activity in the mammal after administration of the test compound; treating the subject with the therapy; administering the BAT imaging agent to the mammal; detecting the imaging agent in the mammal, to obtain an image of BAT in the mammal; processing the image to provide a second measure of BAT levels or activity in the mammal after administration of the test compound; and comparing the first measure of BAT levels or activity in the mammal to the second measure of BAT levels or activity, to detect an increase, decrease, or no change in BAT levels or activity in the mammal; thereby determining the effect of the therapy on BAT levels or activity in the mammal.

In some embodiments, detecting the imaging agent includes detecting fluorescence emission from the imaging agent (e.g., using NIR imaging or thermography); detecting gamma rays (e.g., using Positron emission tomography (PET)); detecting nuclear magnetic resonance (NMR) (e.g., using Magnetic resonance imaging (MRI), nuclear magnetic resonance imaging (NMRI), or magnetic resonance tomography (MRT)); or detecting ultrasonic emissions (e.g., using optoacoustic imaging/photoacoustic imaging, e.g., photoacoustic/thermoacoustic computed tomography (also known as photoacoustic/thermoacoustic tomography, i.e., PAT/TAT) or photoacoustic microscopy (PAM)).

In some embodiments, detecting the imaging agent includes setting a region of interest (ROI); and obtaining an image of the region of interest in the mammal. In some embodiments, the ROI covers one or more of the cervical, supraclavicular, and superior mediastinal areas of the mammal.

In some embodiments, the methods include processing the image to provide a measure of BAT levels or activity in the mammal.

In some embodiments, the methods include one or both of: administering CRANAD-2 to the mammal, and processing the image to provide a measure of BAT activity, and/or administering CRANAD-29 to the mammal, and processing the image to provide a measure of BAT levels.

In some embodiments, the methods include obtaining an image (e.g., of a selected ROI) by detecting fluorescence emission from the imaging agent (e.g., using NIR imaging with an infrared camera or thermography), or detecting ultrasonic emissions (e.g., using optoacoustic imaging/photoacoustic imaging, e.g., photoacoustic/thermoacoustic computed tomography (also known as photoacoustic/thermoacoustic tomography, i.e., PAT/TAT) or photoacoustic microscopy (PAM)); and processing the image to provide information regarding BAT levels or activity in the mammal.

In some embodiments, the methods include scanning the ROI with an infrared camera to obtain an infrared thermographic image of the region of interest in the mammal; processing the image to provide a measure of temperature information; wherein the temperature information provides information regarding BAT levels or activity in the mammal.

In some embodiments of the methods described herein, the BAT imaging agent is a compound of Formula I:

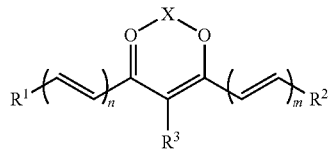

or a pharmaceutically acceptable salt thereof, wherein:
X is —BR$^4$R$^5$ or absent;
R$^1$ is a substituted or unsubstituted aryl or a substituted or unsubstituted heteroaryl;
R$^2$ is a substituted or unsubstituted aryl or a substituted or unsubstituted heteroaryl;
R$^3$ is H or a (C$_1$-C$_6$)alkyl;
R$^4$ and R$^5$ are independently selected from the group consisting of H, halo, and OR$^6$;
R$^6$ is H or a (C$_1$-C$_6$)alkyl; and
n and m are independently 1 or 2.

In some embodiments, the BAT imaging agent is selected from the group consisting of CRANAD-2, CRANAD-3, CRANAD-29, and CRANAD-43.

In some embodiments, the BAT imaging agent includes one or more $^{11}$C, $^{13}$N, $^{15}$O, or $^{18}$F, $^{13}$C, $^{17}$O, or $^{19}$F atoms.

In some embodiments, the imaging agent comprises a positron-emitting radionuclide (e.g., $^{11}$C, $^{13}$N, $^{15}$O, or $^{18}$F, e.g., CRANAD-5F), and the method includes obtaining an image (e.g., of a selected ROI) by detecting gamma radiation from the BAT imaging agent, e.g., using positron emission tomography (PET); and processing the image to provide information regarding BAT levels or activity in the mammal.

In some embodiments, the imaging agent comprises a $^{13}$C, $^{17}$O, or $^{19}$F atom, preferably $^{19}$F, and the method includes obtaining an image (e.g., of a selected ROI) by detecting BAT using an imaging modality suitable for detecting those labeled agents, e.g., for detecting nuclear magnetic resonance (NMR) (e.g., using Magnetic resonance imaging (MRI), nuclear magnetic resonance imaging (NMRI), or magnetic resonance tomography (MRT)); and processing the image to provide information regarding BAT levels or activity in the mammal.

In some embodiments, the methods include comparing the measure of BAT levels or activity to a predetermined value, the predetermined value being a measure of BAT levels or activity in either the same subject, or a measure that represents BAT levels or activity in one or more control subjects. In some embodiments, the predetermined value is a measure of BAT levels or activity in the ROI of the same subject before or after administration of a test compound, wherein the comparison indicates an effect of the test compound on BAT levels or activity.

Also provided herein is the use of a composition described herein in a method of imaging brown adipose tissue (BAT) in a mammal, e.g., for detecting brown adipose tissue (BAT) levels or activity in a mammal.

In some embodiments, mammals that can be evaluated using the methods described herein are humans or non-human mammals, e.g., primates, rodents, dogs, cats, horses, cattle, or other veterinary subjects.

The term "alkyl" includes straight-chain alkyl groups (e.g., methyl, ethyl, propyl, butyl, pentyl, hexyl, heptyl, octyl, nonyl, and decyl) and branched-chain alkyl groups (isopropyl, tert-butyl, isobutyl, and sec-butyl), cycloalkyl (alicyclic) groups (cyclopropyl, cyclopentyl, cyclohexyl, cycloheptyl, and cyclooctyl), alkyl substituted cycloalkyl groups, and cycloalkyl substituted alkyl groups. In certain embodiments, a straight chain or branched chain alkyl has six or fewer carbon atoms in its backbone (e.g., C$_1$-C$_6$ for straight chain; C$_3$-C$_6$ for branched chain). The term C$_1$-C$_6$ includes alkyl groups containing 1 to 6 carbon atoms.

The terms "halo" or "halogen", used alone or in combination with other terms, refers to fluoro, chloro, bromo and iodo.

In general, the term "aryl" includes groups, including 5- and 6-membered single-ring aromatic groups, such as benzene and phenyl. Furthermore, the term "aryl" includes multicyclic ring systems including 8 to 14 members and at least one aryl group, e.g., tricyclic, bicyclic, such as naphthalene and anthracene. In some cases, the multicyclic ring systems can include one or more heteroatoms in the other (non-aryl) rings.

The term "heteroaryl" includes groups, including 5- and 6-membered single-ring aromatic groups, that have from one to four heteroatoms, for example, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include, for example, an alkyl, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, a carbamoyl, a guanidine, an imine, a cyano, a nitro, an azido, a sulfhydryl, an alkylthio, a sulfate, a sulfonate, a sulfamoyl, a sulfonamido, a sulfonyl, a carbocyclyl, a heterocyclyl, an aralkyl, a heteroaralkyl, or an aryl or hateroaryl moiety.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 7A-B. In vivo re-testing of Rhodamine 640 and Phenoxazine 660 and validation of BAT signal using stepwise dissection procedure. (7A) Re-testing of Rhodamine 640 and stepwise dissection images. Image of the intact mouse (left); image after skin and WAT were removed (middle); and image after BAT was removed (right). (7B) Re-testing of Phenoxazine 660 and stepwise dissection images. Image of the intact mouse (left); image after skin and WAT were removed (middle); and image after BAT was removed (right). These images indicated that no significant signals were from BAT in both cases.

FIGS. 8A-H. Time course of CRANAD-2 and CRANAD-3, ex vivo histology and in vitro cell staining (8A) Images of animals injected intravenously with CRANAD-2 at different time points. (8B) Quantitative analysis of interscapular BAT images of animals injected with CRANAD-2 at different time points. (8C) Images of animals injected with CRANAD-3 at different time points after i.v. injection. (8D) Quantitative analysis of interscapular BAT images of animals injected with CRANAD-3 at different time points. (8E) H&E staining for ex vivo BAT tissue. Oil droplets were white, and nuclei were purple blue in original (10×). (8F) Ex vivo histology of animals injected with CRANAD-2 (left) and CRANAD-3 (right). Oil droplets were stained by CRANAD-2, or -3 (red), and nuclei were labeled with DAPI (blue) (10×). Scale bar: 100 micron. (8G) Ex vivo histological images of animals injected with CRANAD-2 with high magnification (40×). DAPI stained nuclei (blue in original), cell autofluorescence (green in original), CRANAD-2 labeled oil droplets (red in original), and merged image of the above channels are shown. Scale bar: 50 micron. (8H) In vitro cell studies with CRANAD-2 (left) and CRANAD-3 (right). Both CRANAD-2 and -3 were able to stain oil droplets in the BMPs-induced BAT cells. Scale bar: 200 micron.

FIGS. 9A-E. (9A) NIR images of probes from the synthesized sub-library. (9B) Quantitative analysis of the top-down screening results of the probes in the curcumin-based sub-library. In the graph each dye has three fluorescent signal readouts. Quantification was conducted with the ratio of the average fluorescent intensity of ROI1/ROI2. (9C) Images of animals injected with CRANAD-43 before (left) and after (right) skin and WAT removal. The images indicated that CRANAD-43 had poor selectivity for BAT over WAT. (9D) Chemical structures of the probes in the sub-library. (9E) Excitation (leftmost line in each figure, red in original) and emission spectra (rightmost line in each panel, blue in original) of the probes in the sub-library.

FIGS. 10A-B. (10A) H&E staining image of ex vivo BAT slice of the animals injected with CRANAD-29 injection. Scale bar: 50 micron. (10B) The time course of CRANAD-29 fluorescence signal after i.v. injection.

FIG. 11. Dose optimization for in vivo studies with CRANAD-29.

FIGS. 14A-C. PET images of a mouse with $^{18}$F-labeled curcumin analogue (CRANAD-5F). (14A) Sagittal image; (14B) coronal image; and (14C) transverse image.

FIG. 14D is the structure of CRANAD-5F, an $^{18}$F-labeled curcumin analogue.

FIGS. 16A-C show the uptake time course of Nile blue with undifferentiated (16A) and differentiated 3T3-L1 cells (16B), (16C) the uptake of Nile blue in differentiated 3T3-L1 cells without (grey bars) and with triglyceride (black bars).

FIGS. 17A-D show limited uptake mechanism studies for CRANAD-29. (17A) The uptake time course of CRANAD-29 in undifferentiated (left) and differentiated 3T3-L1 cells (middle), and the uptake blocking with glutaraldehyde fixed 3T3-L1 cells (right). (17B) Two-photon microscopic images of CRANAD-29 alone (left), with triglyceride competition (right). The CRANAD-29 signal was red in the original image, and autofluorescence of the cells was green in the original image. Scale bar: 100 micron. Apparent loss of CRANAD-29 accumulation in oil droplets was observed in cells treated with triglyceride. (17C) Quantitative analysis images of the cells treated with triglyceride obtained with IVIS imaging system (n=3). (17D) Quantitative analysis images of the cells treated with CD36 specific ligand Hexarelin obtained with IVIS imaging system.

DETAILED DESCRIPTION

Figure 1:
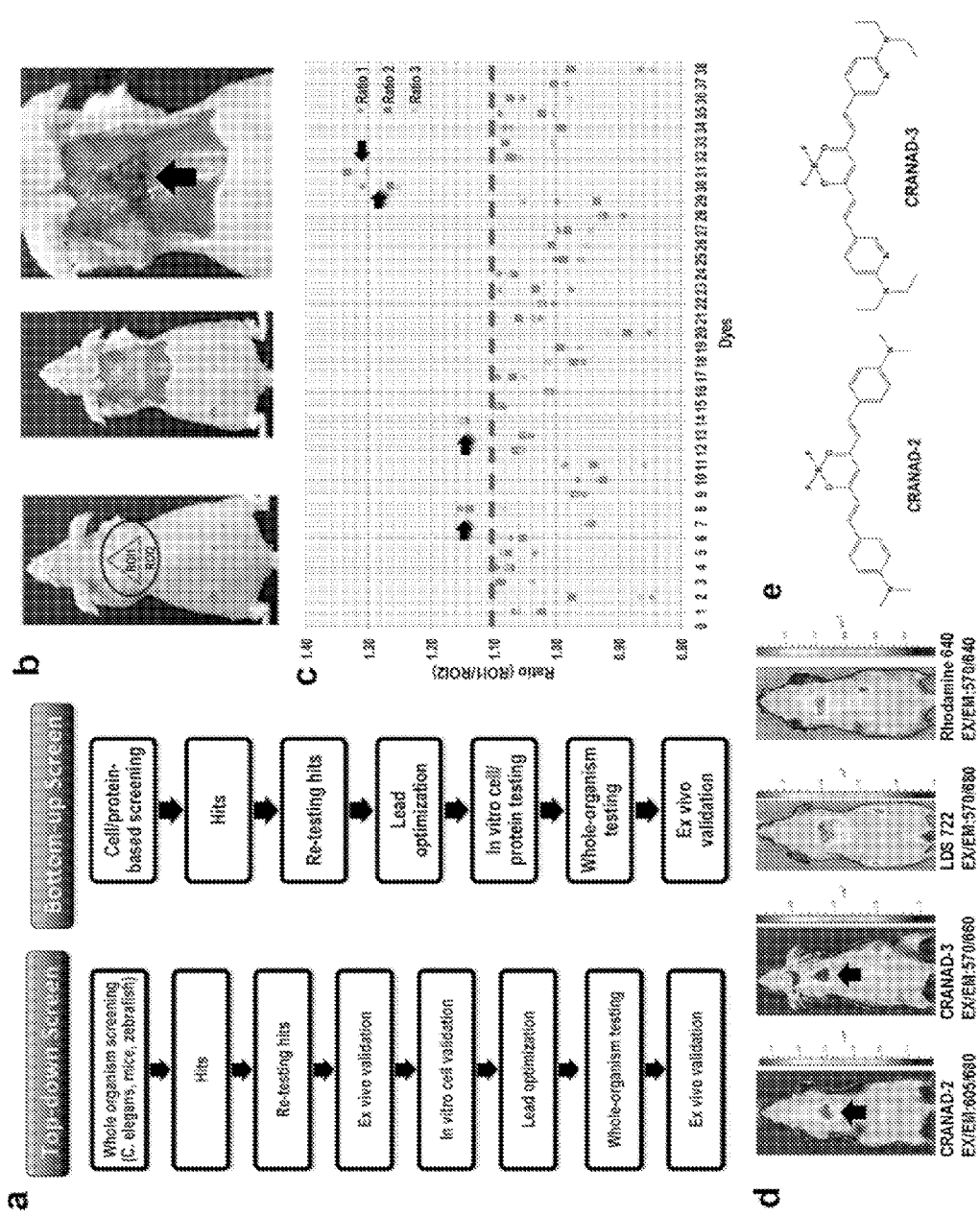
FIGS. 1A-E. Top-down whole-organism screening of a library of 38 fluorescent dyes. (1A) Schematic diagrams of a top-down (left) and a bottom-up screening (right). (1B) Photographs of the locations of interscapular brown adipose tissue (BAT) and white adipose tissue (WAT). In the intact mouse (left), ROI1 (region of interest) in dashed line triangle represents BAT location, and ROI2 (circle) represents the areas of BAT and WAT and adjacent non-adipose tissue area. The WAT that covers BAT can be seen after skin removal (middle), and the triangular shape of BAT (black arrow) can be clearly seen after the removal of skin and WAT (right). (1C) Quantitative analysis of the top-down screening results. In the graph each number represents a dye, and each dye has three fluorescence signal readouts. The quantification was conducted using the ratio of the average fluorescence intensity of ROI1/ROI2, and the threshold was set at 1.10 (dashed line). Four hits (black arrow) were selected for re-testing validation. (1D) Representative near-infrared (NIR) fluorescence images of the screened dyes. CRANAD-2, CRANAD-3, LDS 722 and rhodamine 640 showed apparent signal at the interscapular BAT area. (1E) Chemical structure of CRANAD-2 and -3.

Brown adipose tissue (BAT) is a specialized tissue for thermogenesis in mammals, and it has been considered as a furnace in the body for burning excess calories. BAT function in mammals is to dissipate large amounts of chemical/food energy as heat, thus maintaining energy balance of the whole body [1,2,3]. The most distinct characteristics of BAT include a large number of mitochondria, abundant uncoupling protein-1 (UCP-1) expression, numerous small oil droplets in a single cell, as well as significant vascularization of BAT tissue [4,5,6,7,8]. These characteristics strongly indicate that BAT plays important role in metabolism and energy expenditure.

In humans, BAT is highly abundant in embryonic and early postnatal stages, but is drastically reduced or is considered to have no physiological relevance in adult humans. However, the importance of BAT has recently "re-emerged" in new studies using Positron Emission Tomography (PET). PET images have shown that BAT is still present in adults in the upper chest, neck and other locations [4,5,6]. Recently, Cypess et al. imaged and analyzed 3,640 patients and showed that BMI (body mass index) inversely correlated with the amount of brown adipose tissue, suggesting that BAT is an important target in obesity and diabetes [4]. Other studies also demonstrated that both BMI and body fat percentage had significant negative correlation with BAT, whereas resting metabolic rate correlated positively with BAT [9,10]. Therefore, manipulating mass of BAT is a very attractive approach in anti-obesity and diabetes therapies [11], and the potential approaches include browning of WAT (white adipose tissue), BAT transplantation and BAT mass promotion by drug treatment [6,12,13,14,15,16].

'Browning' is a process of inducing "brown fat-like" changes in white adipose [13,14,15,16]. The appearance of multilocular fat cells and increase of UCP-1 expression in WAT are the two characteristic changes during browning. Recent reports indicated that physical exercise could lead to browning of WAT in animal studies [17,18]. Moreover, several studies have shown that treating white adipocytes either in vitro or in vivo with β3-adrenoceptor agonist (CL 316,243), PPAR-gamma ligand (rosiglitazone) and PRDM16 induces a "browning" process of the white cells [13,14,15,19,20]. These results suggest the potential benefits of browning for obesity treatment.

In addition, there are indications that BAT plays a significant role in ageing [10,21,22], infection [23], inflammation [24], cardiovascular disease, cancer, neurodegenerative disease, and other disorders [6,21,25,26,27].

Given the importance of BAT for various diseases, development of new imaging probes for BAT mass monitoring during the course of pathology and/or therapy is needed. Currently, the most widely used method for BAT imaging is PET imaging with $^{18}$F-FDG. However, BAT imaging with $^{18}$F-FDG requires pretreatment activation (such as cold stress or norepinephrine), and most likely reflects the degree of activation, but not the amount of BAT mass [4,5,26,28, 29,30]. PET imaging probe for BAT thermogenesis has been reported as well [31]. MRI and CT have also been used for imaging BAT [26,32,33,34]. Compared to PET, MRI and SPECT/CT imaging, NIR Fluorescence imaging is significantly more cost-efficient, and is particularly suitable for preliminary in vivo screening in small animals. Nonetheless, to the best of the present inventors' knowledge, reliable NIR fluorescence imaging probes to assess BAT mass are still lacking As shown herein, top-down whole-organism screening was feasible for seeking fluorescent imaging probes for BAT. The testing followed the steps listed in FIG. 1a for top-down screen. Through screening 38 fluorescent dyes using nude mice, it was found that curcumin analogue CRANAD-2 and -3 could highlight the interscapular BAT. Taking CRANAD-2 and -3 as the lead probes, further optimization was conducted by synthesizing a curcumin-based probe library for seeking probes with long excitation and emission wavelengths for better tissue penetrating and better selectivity for BAT. The data indicated that CRANAD-29 represents an excellent probe for in vivo studies and could be used for monitoring BAT mass changes in STZ-induced diabetic mice, and BAT activation after cold exposure treatment. In addition, CRANAD-29 is suitable for monitoring browning of sWAT due to its excellent BAT selectivity over WAT.

Methods of Imaging BAT

Described herein are non-invasive methods for detecting the presence of BAT in a living subject. These methods take advantage of the relative selectivity of the BAT imaging agents described herein, e.g., CRANAD-29, to detect and optionally quantify BAT in a living mammal.

A number of imaging methods can be used with the BAT imaging agents, including any method that detects near infrared emissions, e.g., NIR thermography. General methods for using IR thermography are known in the art, see, e.g., U.S. Pat. Nos. 7,277,744; 6,983,753; and 6,881,584. IR thermographic cameras are also known and are commercially available, e.g., the ThermaCAM® EX320, available from FLIR Systems, Inc., North Billerica, Mass.

In some embodiments, the methods include irradiating the mammal with light of the appropriate wavelength to excite the BAT imaging agent, and detecting emissions therefrom. Table 1 shows the excitation and emissions wavelengths for four exemplary BAT imaging agents.

TABLE 1

| BAT imaging agent | Excitation λ (nm) | Emission λ (nm) |
|---|---|---|
| CRANAD-2 | 605 | 680 |
| CRANAD-3 | 570 | 660 |

TABLE 1-continued

| BAT imaging agent | Excitation λ (nm) | Emission λ (nm) |
|---|---|---|
| CRANAD-29 | 640 | 700 |
| CRANAD-43 | 640 | 700 |
| CRANAD-6 | 620 | 750 |
| CRANAD-19 | 570 | 660 |
| CRANAD-22 | 570 | 655 |
| CRANAD-24 | 600 | 725 |
| CRANAD-25 | 558 | 645 |
| CRANAD-26 | 587 | 637 |
| CRANAD-32 | 575 | 660 |

In some embodiments, the methods include administering a $^{11}$C, $^{13}$N, $^{15}$O, or $^{18}$F labeled derivative of a BAT imaging agent listed in Table 1, and detecting BAT using an imaging modality suitable for detecting gamma ray emissions from those labeled agents, e.g., positron emission tomography (PET); or administering a $^{13}$C, $^{17}$O, or $^{19}$F labeled derivative of a BAT imaging agent listed in Table 1, and detecting BAT using an imaging modality suitable for detecting the spin of those labeled agents, e.g., magnetic resonance imaging (MRI); or detecting ultrasonic emissions (e.g., using optoacoustic imaging/photoacoustic imaging, e.g., photoacoustic/thermoacoustic computed tomography (also known as photoacoustic/thermoacoustic tomography, i.e., PAT/TAT) or photoacoustic microscopy (PAM)).

In these methods, the BAT imaging agent is administered to the mammal in an amount sufficient to be detected by the chosen imaging method. The BAT imaging agent can be administered by any method that is able to deliver a sufficient amount of the imaging agent to the mammal; in preferred embodiments, the BAT imaging agent is administered parenterally, e.g., intravenously or by injection, e.g., intraperitoneal injection.

Methods for processing images to determine levels and/or quantities of BAT based on the detected BAT imaging agent are known in the art and described herein.

In some embodiments, the methods include applying an algorithm to the images to identify emissions from the BAT imaging agent as opposed to emissions from other tissues. For example, a spectral unmixing algorithm as described in Ran and Moore, Mol Imaging Biol. 2012 June; 14(3): 293-300 can be used to dissect fluorescence signals from BAT, WAT (white adipose tissue) and skin.

BAT Imaging Agents

Compounds useful as BAT imaging agents, e.g., for use in the methods described herein, include compounds of Formula (I):

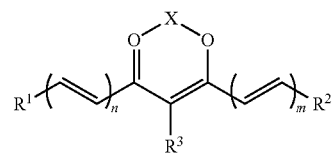

or a pharmaceutically acceptable salt thereof, wherein:
X is —BR$^4$R$^5$ or absent;
R$^1$ is a substituted or unsubstituted aryl or a substituted or unsubstituted heteroaryl;
R$^2$ is a substituted or unsubstituted aryl or a substituted or unsubstituted heteroaryl;
R$^3$ is H or a (C$_1$-C$_6$)alkyl;
R$^4$ and R$^5$ are independently selected from the group consisting of H, halo, and OR$^6$;

$R^6$ is H or a $(C_1-C_6)$alkyl;

n and m are independently 1 or 2.

In some embodiments, $R^4$ and $R^5$ are halo. For example, $R^4$ and $R^5$ can be F. In some embodiments, at least one of $R^4$ and $R^5$ is $^{18}F$. In some embodiments, $R^4$ and $R^5$ are both $^{18}F$.

In some embodiments, $R^1$ and $R^2$ are the same.

In some embodiments, at least one of $R^1$ and $R^2$ is a substituted or unsubstituted heteroaryl. For example, the heteroaryl can be an N-containing heteroaryl. In some embodiments, the N-containing heteroaryl is a substituted or unsubstituted pyridyl or indolyl. For example, the N-containing heteroaryl is selected from the group consisting of:

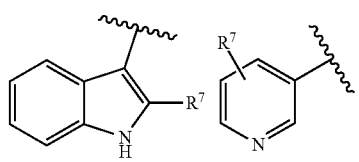

wherein each $R^7$ is independently selected from the group consisting of H, $NR^8R^9$, heterocyclyl, aryl, and heteroaryl; and each $R^8$ and $R^9$ is independently selected from the group consisting of H, $(C_1-C_6)$alkyl, and aryl.

In some embodiments, $R^1$ and $R^2$ are each independently a substituted aryl. In some embodiments, $R^1$ and $R^2$ are each independently a substituted phenyl. For example, $R^1$ and $R^2$ can each independently be a phenyl substituted with a $NR^8R^9$ moiety, wherein each $R^8$ and $R^9$ is independently selected from the group consisting of H and $(C_1-C_6)$alkyl. In some embodiments, $R^1$ and $R^2$ are each independently a substituted or unsubstituted bicyclic or tricyclic ring system including aryl. For example, $R^1$ and $R^2$ can each independently be a substituted or unsubstituted naphthyl or

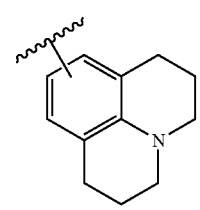

ring system.

In some embodiments, n and m are 1.

Non-limiting examples of a compound of Formula (I) include:

CRANAD-2

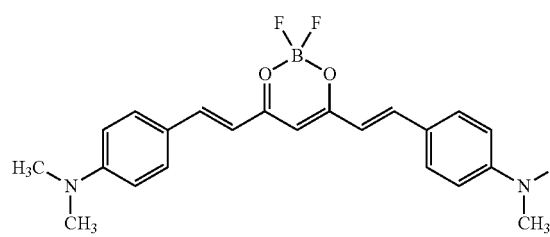

CRANAD-3

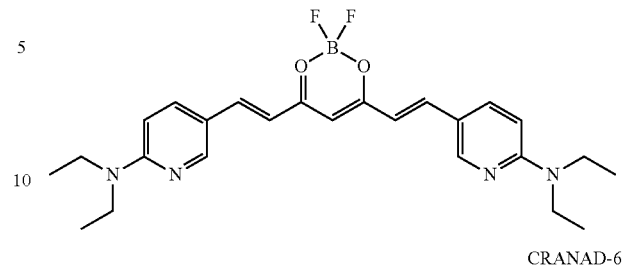

CRANAD-6

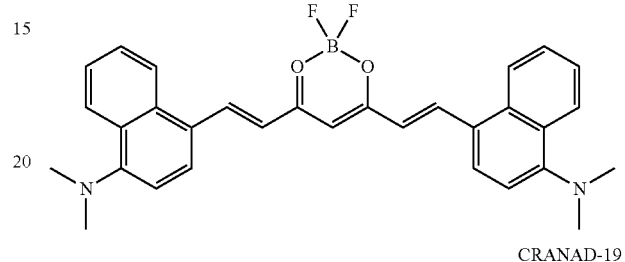

CRANAD-19

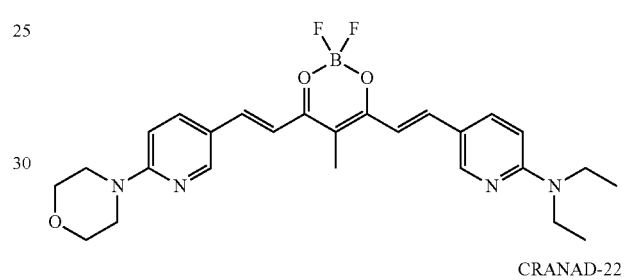

CRANAD-22

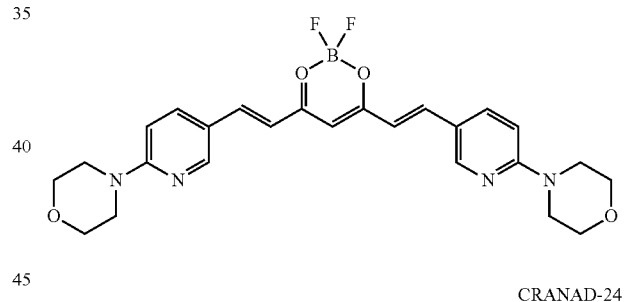

CRANAD-24

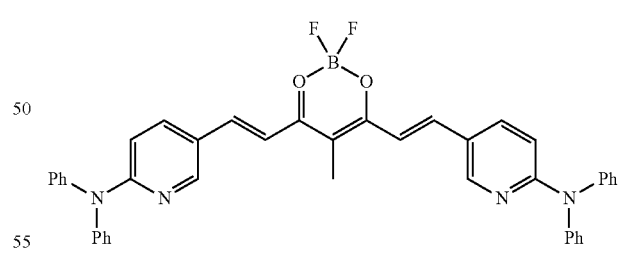

CRANAD-25

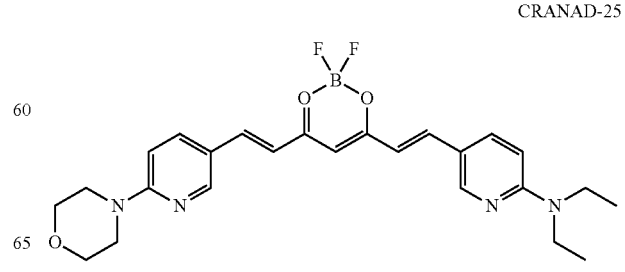

-continued

CRANAD-26

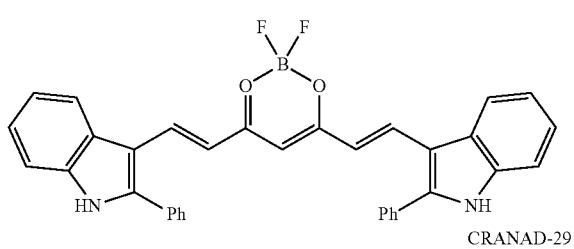

CRANAD-29

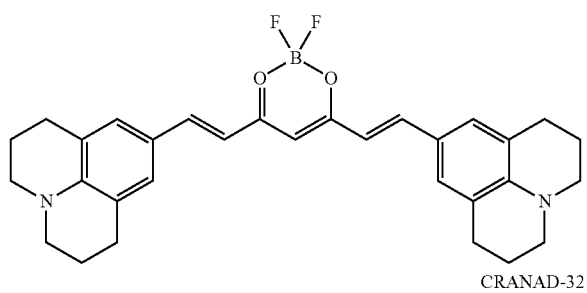

CRANAD-32

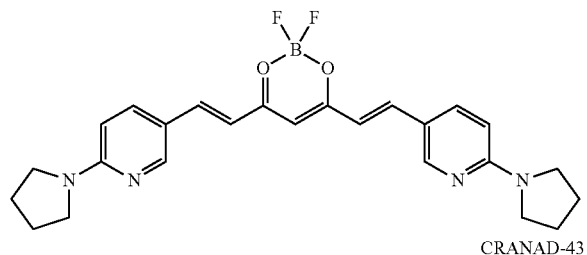

CRANAD-43

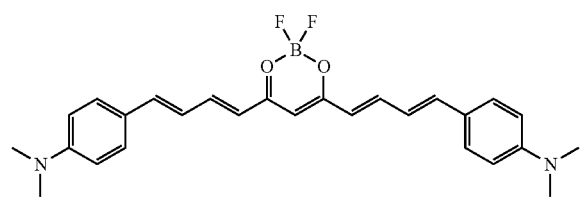

In some embodiments, the BAT imaging agent is CRANAD-2 (synthesis of which is described in Ran et al., J Am Chem Soc. 2009 Oct. 28; 131(42): 15257-15261 and US20110208064, both of which are incorporated herein by reference); CRANAD-3 (synthesis of which is described in Ran et al., Mol Imaging Biol. 2012 June; 14(3): 293-300 and US20110208064, both of which are incorporated herein by reference); CRANAD-43 and CRANAD-29 (CRANAD-29 and -43 were prepared using previously described methods. See, e.g., Ran C. et al. Journal of the American Chemical Society 131: 15257-15261; and Ran C and Moore A (2011) Spectral Unmixing Imaging of Wavelength-Responsive Fluorescent Probes: An Application for the Real-Time Report of Amyloid Beta Species in Alzheimer's Disease. Molecular imaging and biology: MIB: the official publication of the Academy of Molecular Imaging, both of which are incorporated herein by reference. Briefly, crystals of 2,2-difluoro-1,3-dioxaboryl-pentadione crystals were reacted with tetrahydroisoquinoline and the corresponding aromatic aldehyde to prepare the desired compound). Additional synthetic methods, e.g., for CRANAD-2, -3, -5, and -6, can be found in WO 2011014648 and herein.

The BAT imaging agents can be administered in a pharmaceutical composition. Pharmaceutical compositions typically include a pharmaceutically acceptable carrier. As used herein the language "pharmaceutically acceptable carrier" includes saline, solvents, isotonic and absorption delaying agents, and the like, compatible with pharmaceutical administration. Supplementary compounds can also be incorporated into the compositions.

Pharmaceutical compositions are typically formulated to be compatible with its intended route of administration. Examples of routes of administration include parenteral, e.g., intravenous, oral (e.g., inhalation), and transmucosal (e.g., intranasal).

Methods of formulating suitable pharmaceutical compositions are known in the art, see, e.g., Remington: *The Science and Practice of Pharmacy*, 21st ed., 2005; and the books in the series Drugs and the Pharmaceutical Sciences: a Series of Textbooks and Monographs (Dekker, NY). For example, solutions or suspensions used for parenteral administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating a compound as provided herein in the required amount in an appropriate solvent with one or a combination of ingredients enumerated above, as required, followed by filtered sterilization. Generally, dispersions are prepared by incorporating the compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the compound plus any additional desired ingredient from a previously sterile-filtered solution thereof.

Use of the BAT Imaging Methods for Screening and Monitoring BAT in Living Mammals The methods described herein can be used to detect and optionally quantify BAT in living mammals, e.g., humans. Thus, these methods can be used to determine the amount of BAT (mass) or activation in a subject; to detect effects of compounds, e.g., test compounds, on BAT levels (mass or quantity) or activation in a subject; or to monitor changes in BAT levels or activation in a subject, e.g., over time or during the course of a treatment.

Thus, the methods described herein can be used, e.g., to screen potential compounds for efficacy and thereby function as a proximal biomarker. For example, the methods can be used to evaluate test compounds for their effect on BAT levels or activity, e.g., compounds intended to or suspected to increase BAT levels, e.g., anti-obesity treatments and diabetes treatments; compounds that are known or suspected to decrease BAT levels or activity, e.g., toxins, can also be evaluated. The technology enables the measurement of the effectiveness of diets and pharmaceutical agents to increase BAT levels, e.g., to treat obesity or diabetes. The methods can be used to provide an in vivo assessment of BAT inducers.

In addition, these methods can be used in the clinical setting as a non-invasive mechanism to gauge the potential for response to and effectiveness of anti-obesity or diabetes regimens. For example, subjects who have more BAT already present may be more likely to respond to certain treatments than others whose BAT has atrophied. Thus, the methods can be used to identify subjects most likely to benefit from those treatments, e.g., treatments that increase BAT levels or activity.

Based on the outcome of these assays, the subjects can be treated, selected for inclusion in a clinical trial, or stratified within a clinical trial.

Methods of Screening

Included herein are methods for screening test compounds, e.g., polypeptides, polynucleotides, inorganic or organic large or small molecule test compounds, to identify agents that increase BAT levels or activity, e.g., compounds that result in browning of white adipose tissues. Such compounds are expected to be useful in the treatment of disorders associated with metabolism, e.g., obesity, diabetes (e.g., type 2) and the metabolic syndrome.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

A test compound that has been screened by a method described herein and determined to increase BAT levels or activity can be considered a candidate compound. A candidate compound that has been screened, e.g., in an in vivo model of a disorder, e.g., obesity, metabolic syndrome, or diabetes, and determined to have a desirable effect on the disorder, e.g., on one or more symptoms of the disorder, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that increase BAT levels or activity) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating disorders associated with metabolism, e.g., obesity, diabetes (e.g., type 2) and the metabolic syndrome.

Test compounds identified as candidate therapeutic compounds can be further screened by administration to an animal model of a disorder associated with metabolism, e.g., obesity, diabetes (e.g., type 2) and the metabolic syndrome. The animal can be monitored for a change in the disorder, e.g., for an improvement in a parameter of the disorder, e.g., a parameter related to clinical outcome. In some embodiments, the parameter is weight, and an improvement would be weight loss. In some embodiments, the parameter is insulin resistance, and an improvement would be improved insulin sensitivity. In some embodiments, the subject is a human, e.g., a human with obesity, diabetes, or the metabolic syndrome.

EXAMPLES

The invention is further described in the following examples, which do not limit the scope of the invention described in the claims.

Materials and Methods

Fluorescent dyes were purchased from Exciton Inc. (Dayton, Ohio) and Invitrogen. The reagents used for the synthesis were purchased from Aldrich and used without further purification. Column chromatography was performed on silica gel (SiliCycle Inc., 60 Å, 40-63 mm) slurry packed into glass columns. 1H, 13C NMR spectra were recorded at 500 MHz and 125 MHz respectively, and reported in ppm downfield from tetramethylsilane. Fluorescence studies were carried out using a F-4500 Fluorescence Spectrophotometer (Hitachi). Mass spectra were obtained at Harvard University, Department of Chemistry Instrumentation Facility. Microscopic images were acquired with Nikon Eclipse 50i microscope. In vivo NIR imaging was performed using the IVIS® Spectrum animal imaging system (Caliper LifeSciences, Perkin Elmer, Hopkinton, Mass.), and data analysis was conducted using LivingImage® 4.2.1 software.

Example 1

In Vivo Whole-Organism Screening of Fluorescent Probe Library 38 fluorescent dyes from commercial resources and from the inventors' laboratory were screened. Dyes with excitation range of 550-745 nm, emission range of 600-840 nm, and with molecular weight of less than 700 Da (except Cy5.5) (representative dyes are listed in FIG. 1d and the full list is shown in Table 2). Their hydrophobicities were not determined. The library was screened by intravenous tail injection of compounds into nude mice (10μg/mouse). Each dye was imaged with three optimized excitation/emission filter-pairs, and images at one hour after i.v. injection were acquired.

Top-down whole organism screening was performed as follows. Nude mice (nu/nu COX7) were purchased from Massachusetts General Hospital and Balb/c mice were from Jackson Laboratory. All animal experimental procedures were approved by the Institutional Animal Care and Use Committee (IACUC) at Massachusetts General Hospital. Dye stock solutions were prepared in DMSO. The final injection solution (0.1 mg/ml) was freshly prepared in a mixed solution of 20% DMSO, 20% Cremophor EL and 60% saline. Nude mice (n=5) were injected with a 100 μL dye solution via tail vein. For each imaging session, mice were anesthetized with a mixture of oxygen and isoflurane for 5 minutes, and then positioned into the imaging chamber of IVIS® Spectrum in vivo pre-clinical imaging system. Images were acquired at one-hour post-injection using sequence imaging with three excitation/emission filter pairs for each dye.

Hits selection was performed as follows. Hits from cell- or protein-based screening are usually selected by setting certain threshold. In the case of the top-down imaging screening, two methods were used (threshold and visible contrast) to select hits. First, three images obtained with three excitation/emission pairs were selected for each dye. These ex/em pairs were selected from the closest excitation and emission wavelengths of the tested dyes. For instance, 605/660 nm, 605/680 nm, 640/680 nm were selected for image acquisition of Nile blue (625/660 nm). The quantification of contrast for each image was calculated as a ratio of two ROIs (region of interest). $ROI_1$ reflected the average signal from interscapular BAT and $ROI_2$ was the average signal of the area that included BAT and white adipose tissue (WAT) around the interscapular site (FIG. 1b, left). The averaged fluorescent signal of ROI was used instead of the total signal, because the total signal depends on the area of ROI, whereas the averaged signal reflects the density of signal. The ratio of $ROI_1/ROI_2$ could reflect the signal/noise ratio of the tested probe, and could also reflect the selectivity of the probe for BAT over WAT. For each dye, three $ROI_1/ROI_2$ ratios obtained with the three filter pairs were calculated. The mean of the ratios was used as the threshold. If the mean ratio was >1.10, the dye was selected as a potential positive hit (FIG. 1c). Since the contrast of a dye in the top-down screening is in the visible range, the visible contrast around the interscapular BAT area was also tested for the hits with the mean ratio of >1.10. If both mean ratio and the visible contrast were positive, then the hit was subjected to re-testing procedure to validate its reliability as described below.

Figure 6:
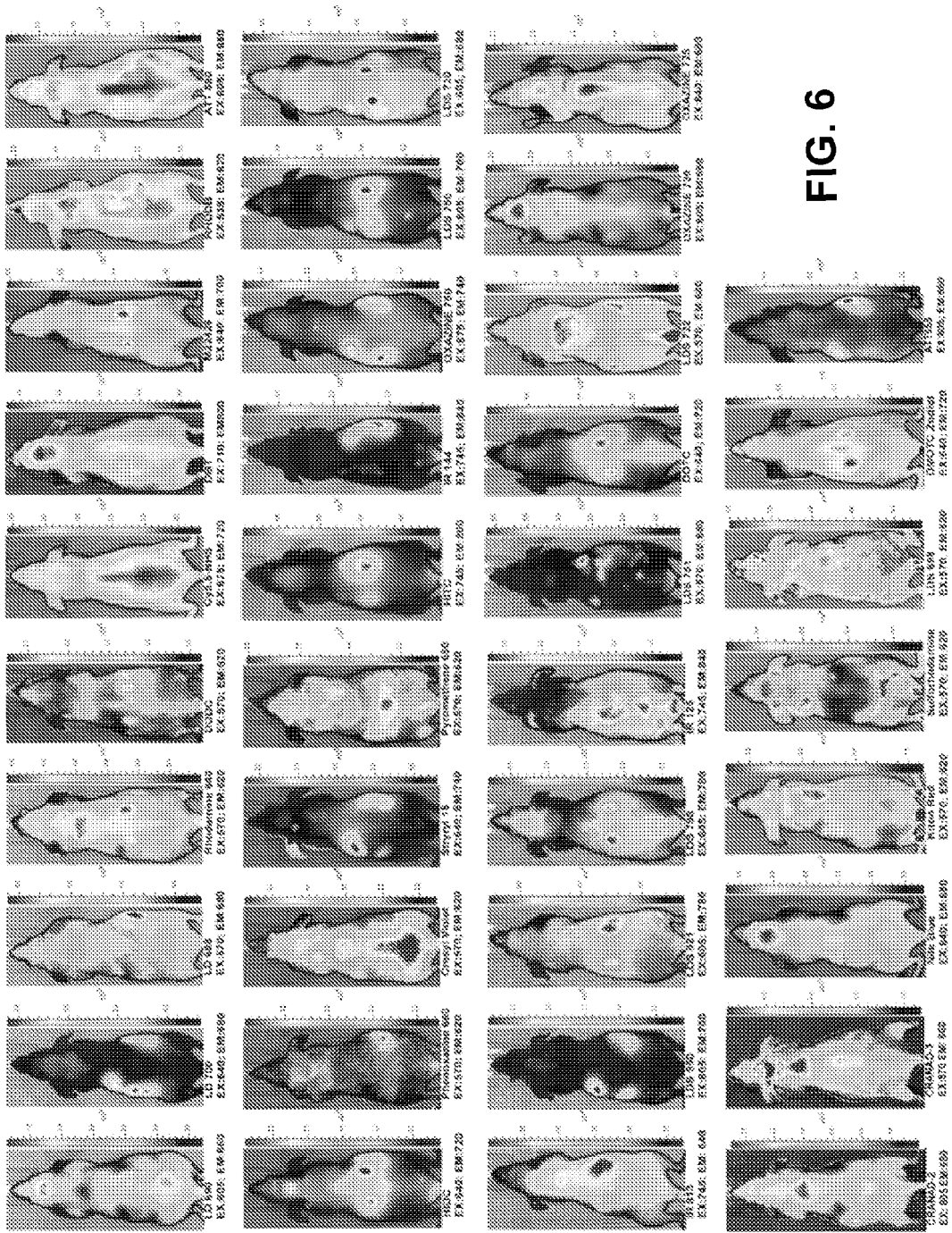
FIG. 6. In vivo NIR images of mice injected with 38 fluorescent dyes. Corresponding excitation and emission wavelengths are listed for each image.

By calculating the mean ratio $ROI_1/ROI_2$ of the dyes, it was found that ratios of CRANAD-2 and CRANAD-3 were the highest (1.28 and 1.32 respectively) followed by LDS722 (1.13) and Rhodamine640 (1.15) (FIG. 1c and Table 2). By reviewing the visible contrast from the images, it was found that CRANAD-2 and CRANAD-3 provided the best contrast and clear triangular contour of interscapular BAT, while LDS722 and Rhodamine640 showed weak contrast and no clear triangular contours (FIG. 1d). In addition, Phenoxazine 660 also showed a weak visible contrast, but its ratio was less than 1.10 (FIGS. 6-7). Images of all thirty-eight dyes tested in vivo are presented in FIG. 6.

TABLE 2

| Dye | Ratio | | | |
|---|---|---|---|---|
| | No 1 | No 2 | No 3 | AVERAGE |
| HITC | 1.07E+00 | 1.02E+00 | 1.06E+00 | 1.05E+00 |
| IR144 | 8.47E−01 | 9.74E−01 | 8.66E−01 | 8.96E−01 |
| OX750 | 1.09E+00 | 1.09E+00 | 1.04E+00 | 1.07E+00 |
| LDS750 | 1.09E+00 | 1.07E+00 | 1.08E+00 | 1.08E+00 |
| LDS730 | 1.03E+00 | 1.08E+00 | 1.09E+00 | 1.07E+00 |
| LDS751 | 1.07E+00 | 1.05E+00 | 1.11E+00 | 1.08E+00 |
| DOTC | 9.48E−01 | 9.44E−01 | 9.52E−01 | 9.48E−01 |
| LDS722 | 1.15E+00 | 1.14E+00 | 1.08E+00 | 1.13E+00 |
| OX720 | 9.55E−01 | 9.70E−01 | 9.69E−01 | 9.65E−01 |
| OX725 | 9.65E−01 | 9.25E−01 | 9.35E−01 | 9.42E−01 |
| LD690 | 9.86E−01 | 9.39E−01 | 8.61E−01 | 9.29E−01 |
| LD700 | 1.05E+00 | 1.06E+00 | 1.06E+00 | 1.06E+00 |
| LD688 | 1.04E+00 | 1.05E+00 | 1.05E+00 | 1.05E+00 |
| Rhodamine640 | 1.15E+00 | 1.15E+00 | 1.15E+00 | 1.15E+00 |
| DODC | 1.08E+00 | 1.09E+00 | 1.10E+00 | 1.09E+00 |
| HIDC | 1.01E+00 | 1.01E+00 | 1.02E+00 | 1.01E+00 |
| Phenox660 | 1.09E+00 | 1.07E+00 | 1.05E+00 | 1.07E+00 |

TABLE 2-continued

| Dye | No 1 | No 2 | No 3 | AVERAGE |
|---|---|---|---|---|
| Cresyl Violet | 9.56E−01 | 9.72E−01 | 1.02E+00 | 9.81E−01 |
| KITON | 9.97E−01 | 9.93E−01 | 9.63E−01 | 9.85E−01 |
| Sulforhodamine | 8.51E−01 | 8.86E−01 | 9.21E−01 | 8.86E−01 |
| LDS698 | 1.03E+00 | 1.06E+00 | 1.04E+00 | 1.04E+00 |
| DMOTC | 1.00E+00 | 1.02E+00 | 1.02E+00 | 1.02E+00 |
| Stryl15 | 9.76E−01 | 1.03E+00 | 1.09E+00 | 1.03E+00 |
| Pyromethene650 | 1.09E+00 | 1.07E+00 | 1.08E+00 | 1.08E+00 |
| Nile Blue | 1.00E+00 | 9.89E−01 | 9.62E−01 | 9.84E−01 |
| RhodamineB | 1.01E+00 | 1.01E+00 | 9.54E−01 | 9.90E−01 |
| ATTO590 | 9.96E−01 | 9.81E−01 | 9.47E−01 | 9.75E−01 |
| ATT655 | 8.92E−01 | 9.24E−01 | 9.32E−01 | 9.16E−01 |
| DBT | 9.98E−01 | 9.35E−01 | 1.06E+00 | 9.96E−01 |
| CRANAD-2 | 1.31E+00 | 1.26E+00 | 1.26E+00 | 1.28E+00 |
| CRANAD-3 | 1.34E+00 | 1.33E+00 | 1.31E+00 | 1.32E+00 |
| Cy5.5 | 1.07E+00 | 1.07E+00 | 1.06E+00 | 1.07E+00 |
| Mito2466 | 1.00E+00 | 1.08E+00 | 1.01E+00 | 1.03E+00 |
| IR813 | 1.08E+00 | 9.91E−01 | 1.08E+00 | 1.05E+00 |
| LDS950 | 1.09E+00 | 1.02E+00 | 1.01E+00 | 1.04E+00 |
| LDS821 | 1.05E+00 | 1.07E+00 | 9.79E−01 | 1.04E+00 |
| LDS798 | 1.00E+00 | 1.00E+00 | 9.88E−01 | 9.98E−01 |
| IR125 | 8.65E−01 | 9.76E−01 | 8.49E−01 | 8.97E−01 |

Example 2

Re-Testing Hits from the Preliminary Screening

Like protein/cell-based screening, hit re-testing experiments were conducted to validate the reliability of this approach. CRANAD-2, -3, LDS 722 and Rhodamine 640 were subjected to re-testing by repeating the above imaging procedure. Images were acquired one hour after probe injection. CRANAD-2 and -3 (chemical structures in FIG. 1e) displayed the highest contrast (FIGS. 2a-c, and FIG. 7) among the re-tested dyes.

Next, stepwise dissection and imaging were performed to track the source of the fluorescence contrast at the interscapular site. Skin and the thin WAT layer that covers BAT were first removed, and then BAT was dissected, and NIR images were captured at each step. Once the skin and WAT were removed, all of the re-tested hits showed significant decrease in signal, indicating that certain contrast originated from skin and WAT. The fluorescence signals from the images of LDS722 acquired before and after BAT removal were not apparently different (FIG. 2a), suggesting no significant fluorescent signal was from BAT. Similar results were observed for Rhodamine640 (FIG. 7a) and phenoxazine660 (FIG. 7b). However, fluorescence signals were higher for CRANAD-2 and -3 when BAT was present compared to the signals when it was dissected (FIG. 2b-c), indicating that the two probes were able to label BAT. The signal contribution from BAT ($R_{(BAT)}$) was roughly estimated using the ratio of fluorescence signals acquired after ($F_{(BAT)}$) and before ($F_{(intact)}$) the first step dissection of skin and WAT. $R_{(BAT)}$ for CRANAD-2 was about 0.26, and 0.51 for CRANAD-3, indicating that the selectivity of these two probes for BAT was low. These data strongly suggested that further optimization of the lead probes was necessary.

Next the time course of CRANAD-2 and CRANAD-3 accumulation in BAT area was investigated. As seen in FIGS. 8a-b, the uptake of CRANAD-2 reached its peak 120 min after injection, was detectable until at least 180 min and was cleared by 720 min. Similarly, the signal of CRANAD-3 reached the uptake peak around one hour, and then gradually washed out (FIG. 8c-d). Accumulation of CRANAD-2 and -3 in BAT was further confirmed with ex vivo histology of the dissected BAT slices, performed as follows. The dissected BAT was fixed with 4% formalin at 4° C. overnight, and then embedded into OCT. BAT tissue was cut into 7 micron thickness slices, washed with PBS buffer, and co-stained with DAPI (Vectra Shield, Vector Lab, Burlingame, Calif.). Images were acquired with fast exposure to capture the dye signal in the oil droplets. To outline cell membrane cell autofluorescence was captured with long exposure after image of the dye signal from oil droplets was already acquired.

Figure 2:
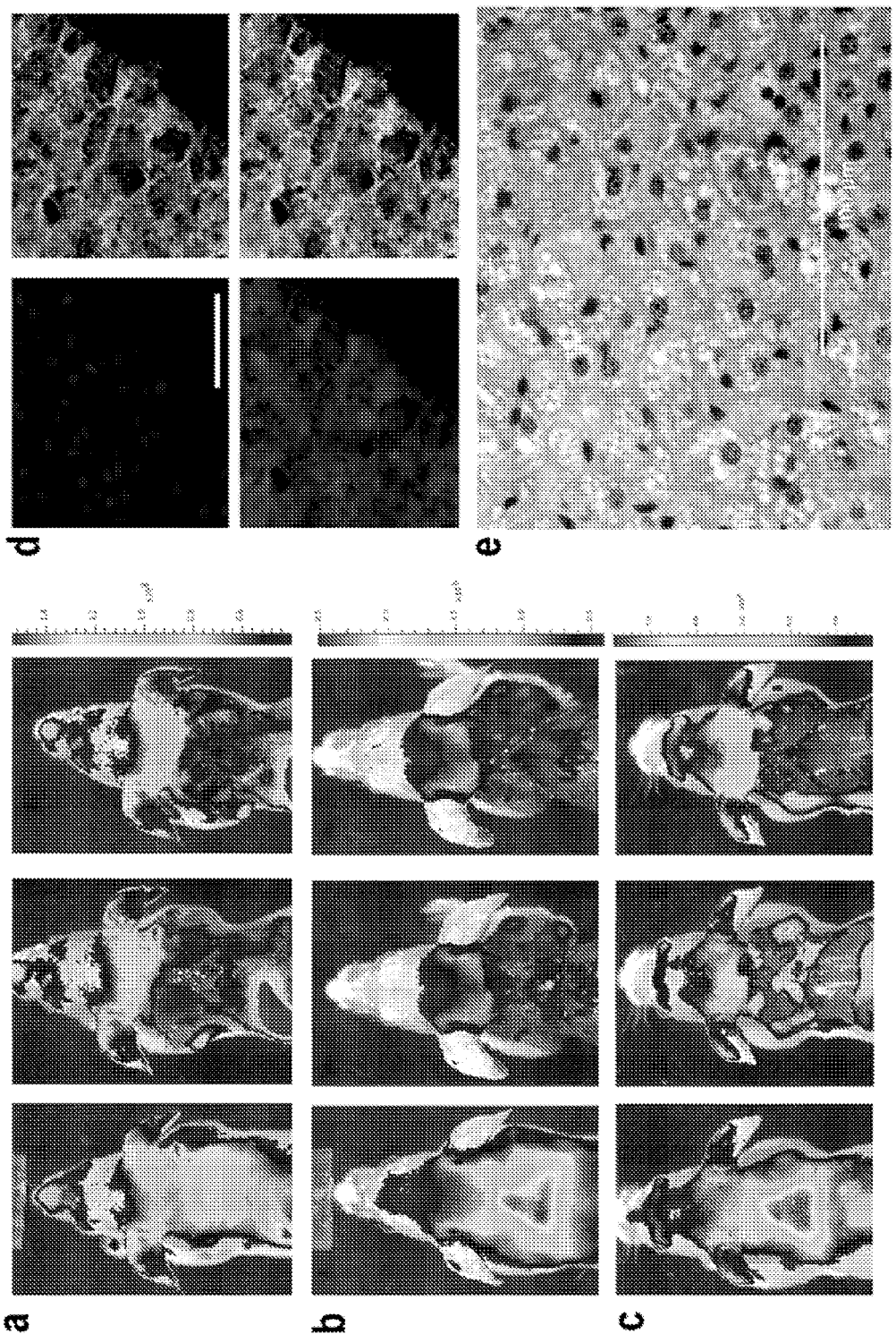
FIGS. 2A-E. Re-testing of the hits and validation of the signal with stepwise dissection and ex vivo histology. (2A-C) Re-testing with LDS 722 (2A), CRANAD-2 (2B), and CRANAD-3 (2C). (left) Images of intact mice, (middle) images after skin and WAT were removed, and (right) images after BAT was dissected. In all cases, the signals were significantly decreased once the skin and WAT were dissected. CRANAD-2 and -3 showed higher signal before BAT removal than after BAT removal (B, C). LDS 722 had no apparent signal difference (A, middle), indicating that LDS 722 was not suitable for labeling BAT in vivo. (2D) Ex vivo histology of CRANAD-3. Oil droplets were stained by CRANAD-3 (red in original), and nuclei were labeled with DAPI (blue in original). Autofluorescence of the cells (green in original) was used to outline cell membranes. Merged image demonstrated that a single cell contains multiple oil droplets (red in original), scale bar: 50 micron. (2E) H&E staining of ex vivo BAT slice of the animal injected with CRANAD-3. Oil droplets were the white round spots and nuclei were in blue purple in the original image. Scale bar: 100 micron.

Fluorescence microscopy indicated that both CRANAD-2 and CRANAD-3 labeled oil droplets in brown adipose cells (FIG. 2d (high resolution) and FIG. 8e-f (low resolution). The shape and size of CRANAD-2 and -3 stained oil droplets resemble those obtained with the gold standard H&E staining (FIG. 2e). To further confirm the capacity of CRANAD-2 and CRANAD-3 for staining BAT, the compounds were incubated with BAT cells, which were induced from wild-type brown preadipocytes by treating them with a cocktail of bone morphogenetic proteins (BMPs) [7,8]. Live cell confocal images indicated that the two probes were able to clearly label oil droplets in BAT cells, and that the droplet size was similar to that in the ex vivo studies with CRANAD-2 and CRANAD-3 (FIG. 8h).

Example 3

Sub-Library Synthesis for Optimizing Lead Probes

Although CRANAD-2 and CRANAD-3 were able to provide certain contrast for BAT in vivo, their excitation and emission wavelengths were still shorter than required for an ideal NIR imaging probe (both excitation and emission >640 nm) [35]. The stepwise dissection results also indicated that their selectivities for BAT were poor. To seek better probes, a sub-library was synthesized based on the structures of the lead probes CRANAD-2 and -3. CRANAD-6, -19, -22, -24, -26, -32 and -43 were synthesized and tested (images and chemical structures, excitation and emission spectra are shown in FIG. 9 a-e). CRANAD-22 and -43 showed the best contrast for in vivo imaging BAT (FIG. 9a). However, the $ROI_1/ROI_2$ ratio of CRANAD-22 was not improved (FIG. 9c). Although CRANAD-43 showed longer excitation and emission wavelengths and higher $ROI_1/ROI_2$ ratio than CRANAD-2, its BAT selectivity was not significantly increased (FIG. 9b).

Figure 3:
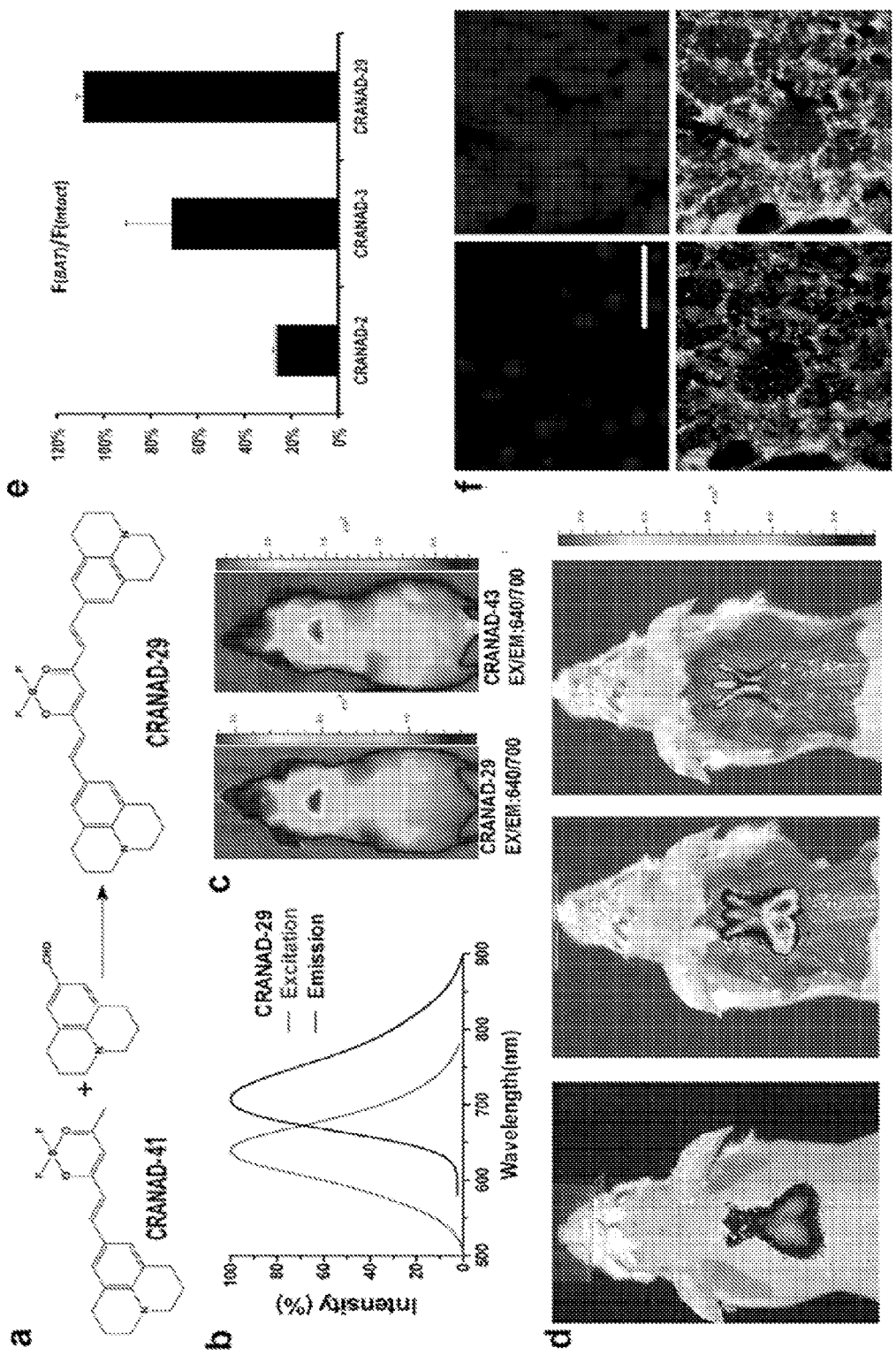
FIGS. 3A-F. Lead optimization, in vivo NIR images and ex vivo histology. (3A) The structure and synthesis of CRANAD-29. (3B) Excitation and emission spectra of CRANAD-29. (3C) Representative in vivo NIR images of CRANAD-29 and CRANAD-43 injected animals. (3D) Stepwise dissection validation the BAT signal after CRANAD-29 injection. There was no significant signal decrease after skin and WAT removal (middle), while the signal disappeared after BAT removal (right). (3E) Comparison of F(BAT)/F(intact) ratio for CRANAD-2, -3, and -29. The ratio for CRANAD-29 was much higher than that for CRANAD-2 and -3, indicating that the selectivity of BAT over WAT was significantly improved after the lead optimization. (3F) Ex vivo histology of CRANAD-29. Oil droplets were stained with CRANAD-29 (red in original), and nuclei were labeled with DAPI (blue in original). Autofluorescence of the cells (green in original) was used to outline the cell membranes (middle), scale bar: 50 micron. Merged image demonstrated that a single cell contains multiple oil droplets.

It has been reported that in some compounds replacement of N,N-dialkylamino-phenyl moiety with julolidine ring could extend excitation and emission wavelengths [36]. Based on CRANAD-2, CRANAD-29 was designed using this strategy (FIG. 3a). To synthesize CRANAD-29, the previously described one step procedure was attempted [37,38], but there was some difficulty in purifying the product. Next, a two-step procedure was used (FIG. 3a), in which an intermediate CRANAD-41 was purified first, and then reacted with the corresponding aldehyde to give CRANAD-29. This probe had significantly longer excitation and emission wavelengths (FIG. 3b). In vivo imaging with CRANAD-29 showed excellent contrast and a very clear contour of BAT at interscapular site (FIG. 3c). CRANAD-29 had also a better $ROI_1/ROI_2$ ratio than CRANAD-2 (1.36 vs 1.28), indicating that it could have a better selectivity for BAT over WAT. Remarkably, after analyzing fluorescence intensity of the signals in the step-wise dissection experiment, CRANAD-29 had an excellent selectivity towards BAT over WAT (FIG. 3d). In addition, CRANAD-29 showed much better BAT selectivity over WAT than CRANAD-2 and -3 (FIG. 3e). Fluorescence signal after skin and WAT removal was even higher than that of the intact animal (FIG. 3d, e).

To further validate the capacity of CRANAD-29 for BAT labeling, ex vivo histological microscopic imaging with CRANAD-29 was conducted. Images clearly indicated that CRANAD-29 was capable of labeling BAT cells, and each cell contained multiple CRANAD-29-stained oil droplets (FIG. 3f). Gold standard H&E staining also provided similar images (FIG. 10a). Time course study indicated that the uptake of CRANAD-29 reached plateau around 2 h after probe injection (FIG. 10b). The injection dose of CRANAD-29 was optimized, and the fluorescence signal reached its plateau at 0.4 mg/kg (FIG. 11). In the following studies, 0.1 mg/kg dose was used.

Figure 12:
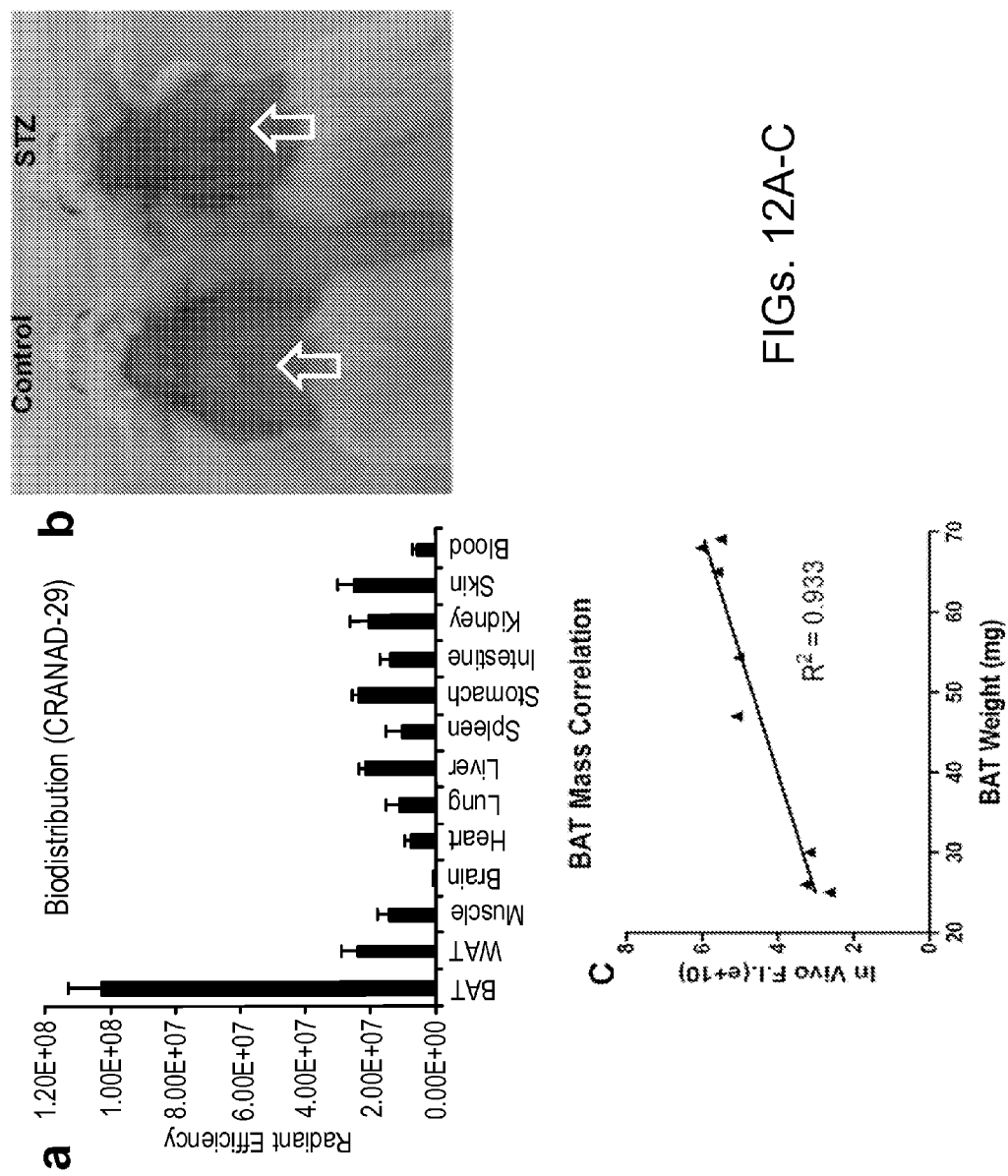
FIGS. 12A-C. (12A) Biodistribution of CRANAD-29 at 4 hours after i.v. injection of CRANAD-29. The data indicated that the highest CRANAD-29 uptake was in BAT. (12B) Representative photographic images of a control mouse (left) and an STZ-treated mouse (right). Arrows point to interscapular BAT. (12C) Correlation between NIR fluorescence signal and the weight of the dissected BAT.

In addition, bio-distribution studies were performed as follows. Mice (n=5) were injected with CRANAD-29 intravenously. BAT and other major organs/tissues were dissected at 4 hours after injection, which were then weighted and subjected to NIR imaging. Fluorescence intensities were normalized to the weight of organ/tissue. The results indicated that interscapular BAT had the highest uptake (FIG. 12a). For these reasons CRANAD-29 was selected as an imaging probe for the proof-of-concept applications described below.

Example 4

Monitoring Interscapular BAT Mass Change in Diabetics Mouse Model

To demonstrate the feasibility of CRANAD-29 for monitoring BAT mass change during diabetes development, a widely used streptozotocin (STZ)-induced type 1 diabetes model was utilized. Several studies have reported that BAT mass is dramatically reduced after STZ treatment [12,39, 40,41]. After STZ treatment interscapular BAT was significantly diminished, and this change was evident even from the light images (FIG. 12b).

Monitoring was performed as follows. Two-month old Balb/c mice (n=5) were injected with STZ (80 mg/kg) for 7 days. When blood glucose levels reached 250 mg/dL on two consecutive days, mice were subjected to NIR imaging with CRANAD-29. Before imaging, the fur around the interscapular area was removed. Images were acquired at pre-injection, as well as 2- and 4-hours after i.v. injection. After imaging, mice were sacrificed, BAT from both groups was dissected, and weighted, and the linear correlation was established between in vivo fluorescence signal and weight of the dissected BATs. The same imaging procedure was conducted with the control group injected with the same volume of saline for 7 days (n=5).

Figure 4:
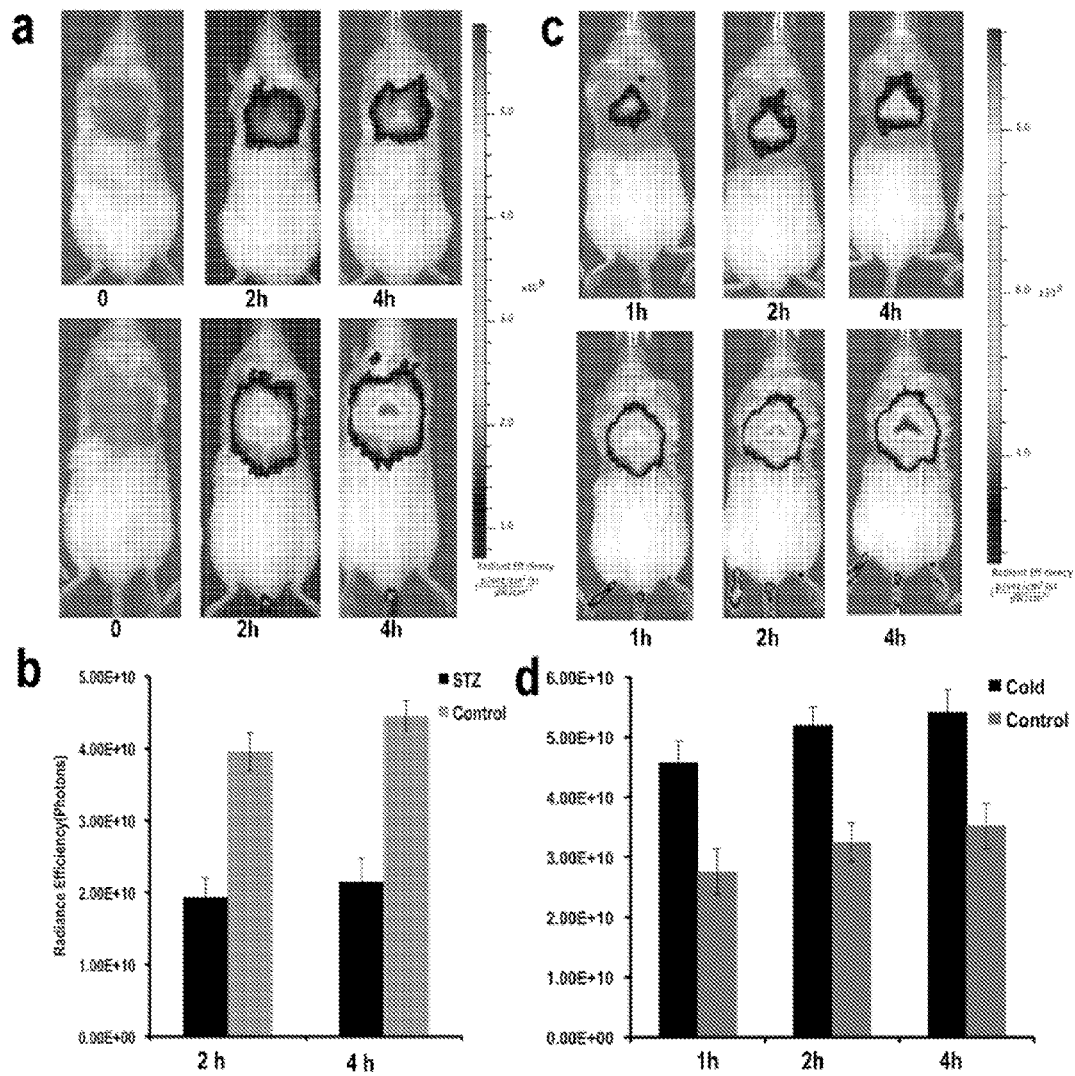
FIGS. 4A-D. Application of CRANAD-29 for monitoring BAT mass change and BAT activation. (4A) Representative NIR images of mice after STZ-treatment (top) and control mice (bottom). (4B) Quantitative analysis of the fluorescence signals in (4A). The signal from STZ-induced diabetic mice was significantly lower than that from control mice. (4C) Representative NIR images of control mice (top) and mice after cold exposure (bottom). (4D) Quantitative analysis of the fluorescence signals in (4C). The signal from mice exposed to cold stress was significantly higher than that of control mice, indicating that CRANAD-29 could be used for monitoring BAT activation.

After CRANAD-29 injection, the fluorescence signal from diabetic mice was significantly lower than that from the control group, reflecting significant BAT mass decrease after STZ treatment (FIG. 4a-b). An excellent direct correlation was found between BAT mass and fluorescence signal in STZ-treated and normal animals (FIG. 12c). These results indicate that fluorescence imaging using CRANAD-29 could be used to report on the relative change of BAT mass.

Example 5

Monitoring BAT Activation Under Cold Exposure

BAT could be activated under various conditions including cold exposure [9,42]. In this report, whether CRANAD-29 could be used to monitor BAT activation under these conditions was investigated as follows. Two-month old balb/c mice (n=5) were placed in a 4° C. cold room for 2 hours before i.v. injection of CRANAD-29. Images were acquired at 1-, 2-, 4-hours after probe injection, and mice were placed in the cold room between imaging sessions. Control mice (n=5) were placed in a 25° C. room. Images were captured at the same time points after CRANAD-29 injection.

Animals subjected to cold exposure displayed 1.65-, 1.59-, and 1.53-fold higher signal after CRANAD-29 administration than the control group at 1-, 2-, and 4-hours after probe injection, indicating that CRANAD-29 could be used for monitoring BAT activation (FIG. 4c,d).

Example 6

Monitoring the Browning of Subcutaneous WAT (sWAT)

Browning of white adipose tissue could be achieved through several approaches, including small molecules stimulation such as β3-adrenoceptor agonist (CL 316,243), PPAR_gamma ligand (rosiglitazone), treatment with hormones and cytokines, and genetic manipulation [13,14,15, 19,20,43]. As a proof-of-concept, CL 316,243 was used to treat mice for establishing the browning model.

Figure 5:
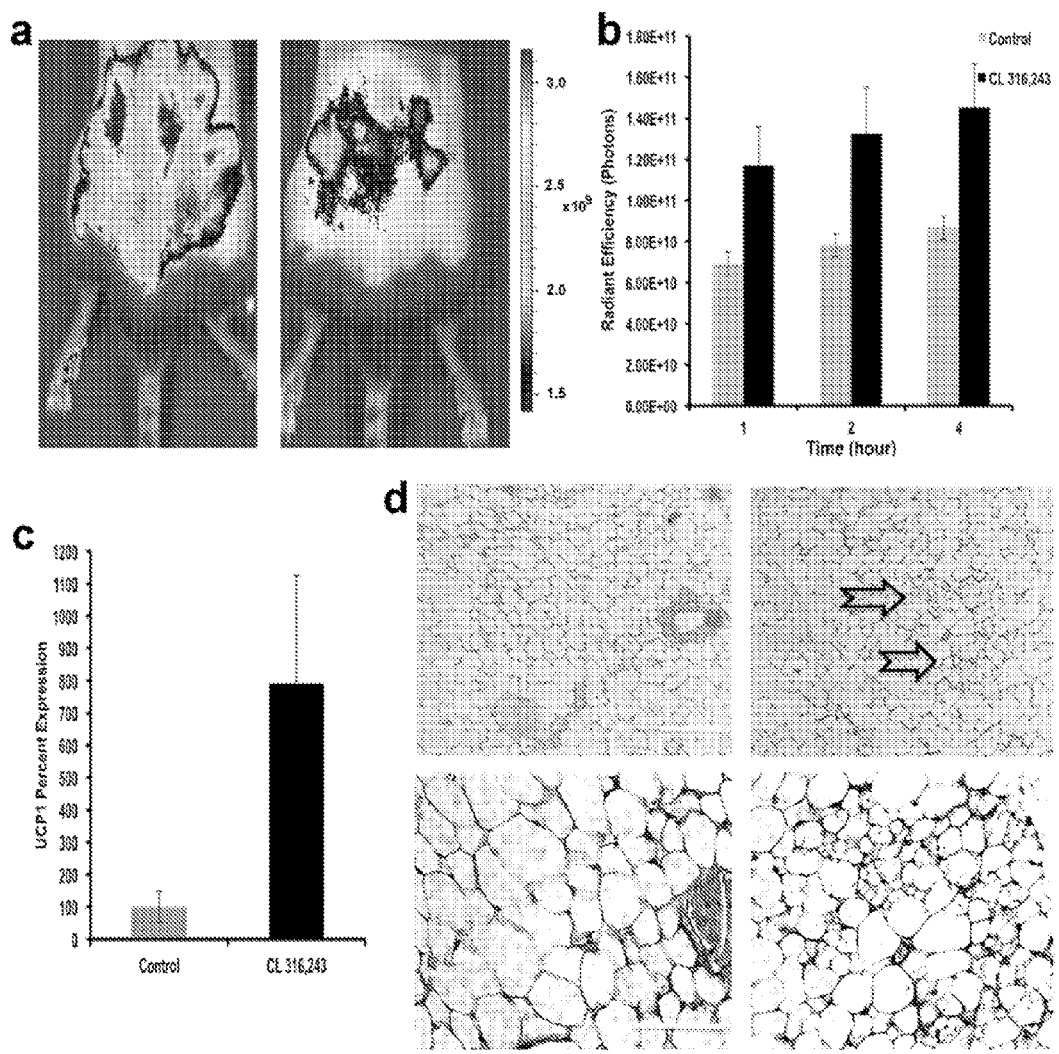
FIGS. 5A-D Application of CRANAD-29 for monitoring the browning of sWAT. (5A) Representative NIR images of a mouse after 12-day CL 316,243 treatment (left) and a control mouse (right) at 4 hours post CRANAD-29 injection. (5B) Quantitative analysis of the fluorescence signals at 1, 2, and 4 hours post CRANAD-29 injection. (5C) UCP-1 expression in sWATs of CL 316,243 treated mice and control mice. (5D) H&E staining of sWAT slices of a CL 316,243-treated mouse (right) and a control mouse (left). Black arrows indicated the areas containing multilocular fat cells. Top row: low resolution (10×), scale bar: 200 micron, bottom row: high resolution (40×), scale bar: 100 micron.
Figure 13:
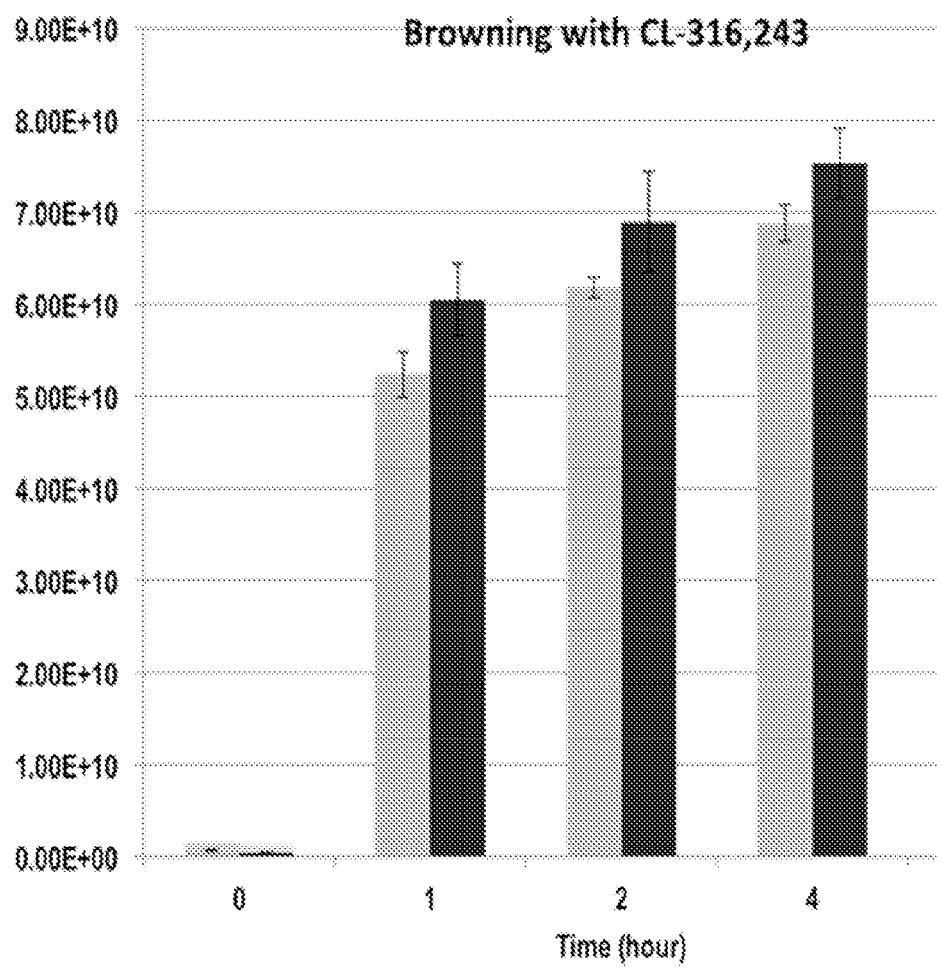
FIG. 13. Quantitative analysis of the fluorescent signals of interscapular BAT at 1, 2, and 4 hours post CRANAD-29 injection for CL 316,243 treated group (black bars) and the control group (grey bars).

Two-month old C57BL6 mice (n=5) were i.p. injected CL 316,243 (100 uL, 1.0 mg/kg) for 12 days, and the control mice (n=5) were i.p. injected with saline. On the 13$^{th}$ day, both groups were imaged after i.v. injection of CRANAD-29. Images were acquired at 1-, 2-, 4-hours after the probe injection. After the last imaging session, inguinal sWAT were dissected after scarification of the mice, and the dissected sWAT tissue was subjected to qPCR for UCP-1 expression and H&E staining After 12 days of CL 316,243 injection, the signal of CRANAD-29 was significantly higher around the inguinal subcutaneous WAT in the treated group than that of the control group (FIG. 5a,b). This result was coherent with UCP-1 expression and H&E staining results (FIG. 5c,d). The UCP-1 mRNA level was 7.9-fold higher in the treated mice than that of the control group (FIG. 5c), and H&E staining showed cells with multilocular lipid droplets in the sWAT slice of the treated mice (FIG. 5d). In addition, a higher fluorescent signal was observed from the interscapular BAT area in the treated group than that of the control group (FIG. 13).

Example 7

PET Imaging with Curcumin Analogue

Although NIR fluorescent imaging is best for small animals, PET and other imaging modalities are more optimal for non-invasive translational imaging in larger mammals including humans. Thus an $^{18}$F labeled curcumin analogue (CRANAD-5F) was synthesized (structure shown in FIG. 14D) as described in Example 8, below.

PET imaging was conducted with a microPET P4 system (Concorde Microsystems Incorporated, Knoxville, Tenn., USA). The imaging parameters of this system are in-plane and axial resolution of 1.2 mm full width at half maximal count. Prior to PET imaging, mice were anesthetized with isoflurane/O$_2$, and then fixed to the imaging table with a custom-fabricated mold. Injection catheter was placed in tail vein for administration of the radiotracer. Subsequently, CRANAD-5F[18] (100-180 µCi) was injected into the tail vein and volumetric dynamic data were acquired in list-mode format for 120 min. Imaging data were corrected for uniformity, attenuation, decay, and acquisition time. PET images were reconstructed using filtered back projection with a Ramp filter (cutoff value of 0.5). The software, ASIPro 6.0, was provided by the microPET manufacturer.

As shown in FIGS. 14A-C, in vivo PET imaging with CRANAD-5F clearly highlighted BAT at the interscapular site, pointing to the feasibility of using curcumin analogues for PET imaging for the possible future translational imaging studies.

Example 7

Synthesis of CRANAD-6, -19, -22, -24, -25, -26, -29, -32 and -43

These compounds were prepared according to previously reported procedures [37,38]. Briefly, the 2,2-difluoro-1,3-dioxaboryl-pentadione crystals (0.075 g, 0.5 mmol) were dissolved in acetonitrile (1.5 ml), followed by the additions of acetic acid (0.1 ml), tetrahydroisoquinoline (0.02 mL, 0.15 mmol), and aromatic aldehyde (1.0 mmol). The resulted solution was stirred at 60° C. overnight. A black residue obtained after removing the solvent was subjected to flash column chromatography to give a dark powder.

CRANAD-6: yield 15.2%. $^1$H NMR (CDCl$_3$) δ(ppm) 2.98 (s, 12H), 6.10 (s, 1H), 6.75 (d, 2H, J=15.0 Hz), 6.98 (d, 2H, J=7.5 Hz), 7.51 (t, 2H, J=7.0 Hz), 7.58 (t, 2H, J=7.0 Hz), 7.85 (d, 2H, J=7.5 Hz), 8.16 (d, 2H, J=8.0 Hz), 8.27 (d, 2H, J=8.0 Hz), 8.83 (d, 2H, J=15.0 Hz); $^{13}$C NMR (CDCl$_3$) δ(ppm) 44.6, 102.2, 113.0, 119.4, 123.6, 124.6, 125.30, 125.38, 127.2, 127.3, 127.7, 133.4, 142.9, 155.2, 178.6; $^{19}$F NMR (CDCl$_3$) δ(ppm) 140.933, 140.993; ESI-MS (M-H) m/z=510.3.

CRANAD-19: yield 21.5%. $^1$H NMR (CDCl$_3$) δ(ppm) 2.09 (s, 3H), 3.61 (t, 8H, J=4.5 Hz), 3.75 (t, 3H, J=4.5 Hz), 6.58 (d, 2H, J=10.5 Hz), 6.78 (d, 2H, J=15.5 Hz), 7.70 (dd, 2H, J=10.5, 2.0 Hz), 7.92 (d, 2H, J=15.5 Hz), 8.33 (d, 2H, J=2.0 Hz); $^{13}$C NMR (d-DMSO) δ(ppm) 11.31, 45.12, 66.33, 107.23, 107.61, 114.77, 120.50, 137.15, 144.64, 153.14, 159.88, 176.63; $^{19}$F NMR (CDCl$_3$) δ(ppm) 143.72, 143.78; ESI-MS (M$^{+1}$) m/z=511.3.

CRANAD-22: Both aromatic aldehydes were added at the same time, and CRANAD-22 was isolated from the mixture. Yield 28.9%. $^1$H NMR (CDCl$_3$) δ(ppm) 1.17 (t, 6H, J=7.5 Hz), 3.54 (q, 4H, J=7.5 Hz), 3.60 (t, 4H, J=5.0 Hz), 3.74 (t, 4H, J=5.0 Hz), 5.85 (s, 1H), 6.37 (d, 1H, J=16.0 Hz), 6.42 (d, 1H, J=16.0 Hz), 6.46 (d, 1H, J=8.5 Hz), 6.58 (d, 1H, J=8.5 Hz), 7.61 (d, 1H, J=7.5 Hz), 7.66 (d, 1H, J=7.5 Hz), 7.84 (d, 1H, J=16.0 Hz), 7.87 (d, 1H, J=16.0 Hz), 8.30 (s, 2H); $^{13}$C NMR (CDCl$_3$) δ(ppm) 12.92, 43.14, 44.98, 66,56, 101.25, 106.21, 106.55, 114.81, 116.85, 118.18, 120.02, 135.66, 136.00, 143.04, 145.03, 151.67, 153.14, 158.63, 159.74, 177.57, 178.80; $^{19}$F NMR (CDCl$_3$) δ(ppm) 141.80; ESI-MS (M$^+$) m/z=483.2.

CRANAD-24: yield 43.7%. $^1$H NMR (CDCl$_3$) δ(ppm) 5.98 (s, 1H), 6.53 (d, 2H, J=15.5 Hz), 6.98 (d, 4H, J=10.5 Hz), 7.16-718 (m, 12H), 7.32-7.38 (m, 8H), 7.43 (d, 4H, J=10.5 Hz), 7.95 (d, 2H, J=15.5 Hz); $^{13}$C NMR (CDCl$_3$) δ(ppm) 101.73, 117.37, 120.53, 124.84, 126.01, 126.78, 129.66, 130.68, 146.28, 146.35, 151.27, 178.61; $^{19}$F NMR (CDCl$_3$) δ(ppm) 141.38, 141.44; ESI-MS (M-H) m/z=658.3.

CRANAD-26: yield 6.8%. $^1$H NMR (d-DMSO) δ(ppm) 6.49 (s, 1H), 6.93 (d, 2H, J=15.5 Hz), 7.31 (m, 4H), 7.53 (d, 2H, J=7.0 Hz), 7.56-7.66 (m, 10H), 8.05 (d, 2H, J=15.5 Hz), 8.10 (d, 2H, J=8.0 Hz), 12.27 (br, 2H); $^{13}$C NMR (d-DMSO) δ(ppm) 101.61, 110.90, 113.12, 115.81, 121.43, 122.72, 124.72, 126.19, 129.58, 130.24, 130.35, 130.87, 137.63, 139.45, 147.49, 177.39; $^{19}$F NMR (d-DMSO) δ(ppm) 139.53, 139.55; ESI-MS (M$^{+1}$) m/z=555.2.

CRANAD-29: This compound was synthesized from CRANAD-41, yield 9.0% (based on CRANAD-41). $^1$H NMR (CDCl$_3$) δ(ppm) 1.89 (quit, 8H, J=6.0 Hz), 2.67 (t, 8H, J=6.0 Hz), 3.21 (t, 8H, J=5.5 Hz), 5.71 (s, 1H), 6.28 (d, 2H, J=15.5 Hz), 6.98 (s, 4H), 7.75 (d, 2H, J=15.5 Hz); $^{13}$C NMR (CDCl$_3$) δ(ppm) 21.37, 27.65, 50.09, 100.66, 113.82, 121.13, 121.54, 129.03, 146.20, 146.54, 176.90; $^{19}$F NMR (CDCl$_3$) δ(ppm) 142.87, 142.93; ESI-MS (M$^+$) m/z=515.3.

CRANAD-32: yield 13.7%. $^1$H NMR (CDCl$_3$) δ(ppm) 1.95 (m, 8H), 3.48 (m, 8H), 6.25 (s, 1H), 6.58 (d, 2H, J=9.5 Hz), 6.84 (d, 2H, J=15.5 Hz), 7.85 (d, 2H, J=15.5 Hz), 7.99 (dd, 2H, J=9.5, 1.5 Hz,), 8.47 (d, 2H, J=1.5 Hz); $^{13}$C NMR (CDCl$_3$) δ(ppm); $^{19}$F NMR (CDCl$_3$) δ(ppm); ESI-MS (M$^+$) m/z=465.2.

CRANAD-41: yield 37%. $^1$H NMR (CDCl$_3$) δ(ppm) 1.89 (m, 4H), 2.14 (s, 3H), 2.66 (t, 4H, J=6.0 Hz), 3.24 (t, 4H, J=6.0 Hz), 5.72 (s, 1H), 6.20 (d, 1H, J=15.0 Hz), 7.00 (s, 2H), 7.86 (d, 1H, J=15.0 Hz); $^{13}$C NMR (CDCl$_3$) δ(ppm) 21.18, 23.74, 27.60, 50.18, 100.10, 111.47, 120.76, 121.24, 129.95, 147.35, 150.49, 180.24, 185.20; $^{19}$F NMR (CDCl$_3$) δ(ppm) 141.12, 141.18; ESI-MS (2M-2H+Na) m/z=685.3.

CRANAD-43: This compound was synthesized by following similar procedure as for CRANAD-29. 3.9%. $^1$H NMR (CDCl$_3$) δ(ppm) 2.97 (s, 8H), 3.01 (s, 4H), 5.77 (s, 1H), 6.05 (d, 1H, J=15.0 Hz), 6.37 (d, 1H, J=15.0 Hz), 6.60 (d, 2H, J=9.0 Hz), 6.61 (d, 2H, J=9.5 Hz), 6.72 (dd, 2H, J=12, 15 Hz), 6.93 (d, 1H, J=15 Hz), 7.34 (d, 2H, J=9.0 Hz), 7.43 (d, 2H, J=9.5 Hz), 7.72 (dd, 2H, J=12, 15 Hz), 7.89 (d, 1H, J=15 Hz); $^{13}$C NMR (CDCl$_3$) δ(ppm) 40.10, 40.16, 101.17, 111.90, 111.99, 114.85, 121.16, 122.24, 129.67, 131.52, 145.36, 147.26, 147.61, 152.76; $^{19}$F NMR (CDCl$_3$) δ(ppm) 142.09, 142.18; ESI-MS (M-H) m/z=462.3.

Example 8

Synthesis of CRANAD-5F

The $^{18}$F labeled curcumin analogue (CRANAD-5F) (structure shown in FIG. 14D) was synthesized as in WO 2011014648, e.g., using a modified procedure of that previously reported for the preparation of CRANAD-2 (Ran et al. (2009) J Am Chem Soc 131:15257-15261; and US 2011/0208064). CRANAD-5F is an analogue of CRANAD-2.

Briefly, an aqueous $^{18}$F solution (about 1.0 ml) was directly delivered from the target to a 5-ml V-vial containing K$_2$CO$_3$ (1.0 mg) and Kryptofix 2.2.2 (2.0 mg). Water was evaporated under a N$_2$ flow at 130° C. during a period of 15 min, and dry acetonitrile (1.5 ml×4) was used for azeotropic distillation to remove residual water. To the dried $^{18}$F/K2.2.2 vial was added a solution of CRANAD-9 (2.0 mg) in dry DMSO (0.2 ml). The vial was vortexed for 30 s and then heated at 120° C. for 10 min. After cooling for 4 min the reaction mixture was diluted with water (2.5 ml), filtered through a C18 Sep-Pak, and washed with water (3×3 ml). The Sep-Pak was then washed with methylene chloride (3×3 ml), and the methylene chloride filtrate was dried with MgSO$_4$. The resulting methylene chloride solution was concentrated to 1 ml, which was further purified with HPLC through a silica column (20% ethyl acetate, 20% methylene chloride and 60% hexane). The synthesis was finished within 2 hours, and the radiochemical yield was 2%. See also Shoup et al., J Nucl Med. 2011; 52 (Supplement 1):1538.

Example 9

Uptake Mechanism Studies for CRANAD-2

Movement of a small molecule across a cell membrane can be mediated by simple diffusion and facilitated diffusion/transport. Fast simple diffusion often leads to non-specific uptake, and highly hydrophobic compounds are prone to cross the cell membrane through the fast simple diffusion (Alberts, B.; Johnson, A.; Lewis, J. *Molecular Biology of the Cell;* 4th ed.; Garland Science: New York, 2002.). From the screening described herein, most of the tested 38 dyes were highly hydrophobic. CRANAD-2, -3, and Nile blue provided positive or negative contrasts, suggesting that the simple diffusion caused by high hydrophobicity was not the only factor in determining the BAT contrast, and facilitated diffusion/transport of CRANAD-2 and -3 into BAT was also very possible.

To investigate the facilitated diffusion of CRANAD-2, the time courses of CRANAD-2 uptake in 3T3-L1 cells were compared before and after differentiation. Two-photon imaging for 3T3-L1 cells was performed as follows. Fibroblast 3T3-L1 cells were differentiated following the protocol provided by Zenbio, Inc. (protocol No. ZBM0009.02). Ten microliters of CRANAD-2 (250 µM in DMSO) was added to the differentiated cells (1.0 ml). Cells were imaged after 10 min of incubation. A 940 nm laser was first used to capture an image for CRANAD-2 in 570-620 nm channel (Prairie Two-photon microscope, Middleton, Wis.). Next, the laser was tuned to 750 nm to capture autofluorescence of the cells to outline cell morphology.

For triglyceride competition, stock solutions of CRANAD-2 (250 µM) and triglyceride (5 mM) in DMSO were prepared. Before imaging, 10 µl of the stock solution was added to the cells.

IVIS imaging of 3T3-L1 cells with CRANAD-2 was performed as follows. To a 6-well plate seeded with preadipocytes or differentiated adipocytes, a 10 µL solution of CRANAD-2 (250 µM in DMSO) was added. The plate was subjected to imaging using IVIS imaging system with Ex=605 nm, Em=660 nm before and after addition of CRANAD-2. For triglyceride competition, the same protocol for two-photon imaging was used. The images were acquired at 20 min after addition of CRANAD-2. Studies were performed in triplicate.

Figure 15A:
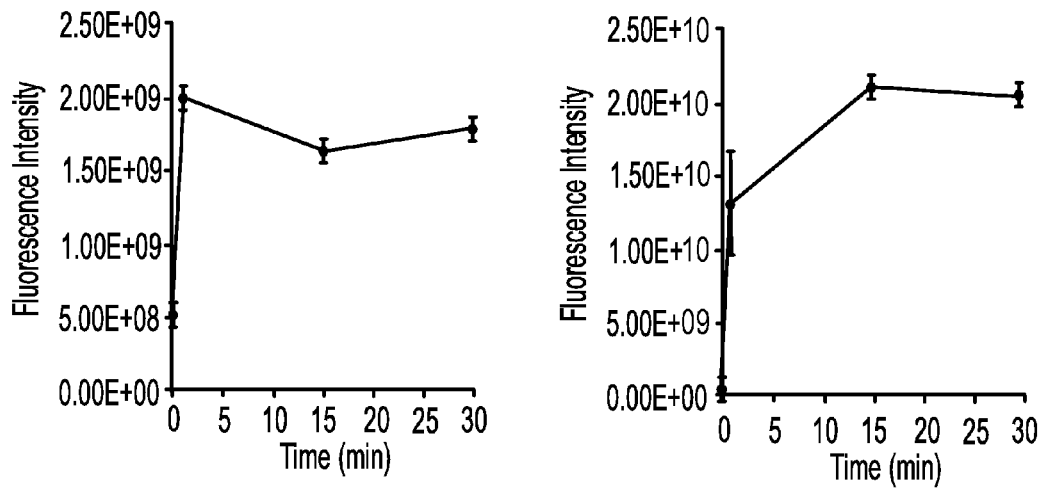
FIGS. 15A-E show the results of uptake mechanism studies. (15A) The uptake time course of CRANAD-2 in undifferentiated (left) and differentiated 3T3-L1 cells. The fast uptake phase indicates simple diffusion. (15B) Two-photon microscopic images of CRANAD-2 alone (left), with triglyceride competition (right). In the original image, Red was the CRANAD-2 signal, and green was autofluorescence of the cells. Scale bar: 100 micron. Apparent loss of CRANAD-2 accumulation in oil droplets was observed in triglyceride-treated cells. (15C) Representative quantitative images of the cells treated with triglyceride obtained with IVIS imaging system for CRANAD-2 and Nile blue. (15D) Quantitative analysis of the images of CRANAD-2 (n=3) in (15C). (15E) Two-photon cell imaging of 3T3-L1 adipose cells with Nile blue (left: Nile blue in the cytoplasm, middle: Nile blue in oil droplets, right: merged). Scale bar: 50 micron.

The uptake reached its maximal within 1 minute with undifferentiated 3T3-L1 cells (FIG. 15A, left), indicating that the uptake is most likely due to simple diffusion. For differentiated 3T3-L1 cells, the uptake reached 62% of the maximal within 1 minute, and reached the plateau at 15 minute (FIG. 15A, right), suggesting that partial accumulation of CRANAD-2 is likely due to facilitated diffusion mediated by receptors/transolcases expressed in differentiated 3T3-L1 cells, but not in preadipocytes. Nile blue, a negative contrast probe, rapidly reached the plateau in both differentiated and undifferentiated 3T3-L1 cells, suggesting that its uptake was primarily due to the fast simple diffusion (FIGS. 16A-B).

Figure 15B:
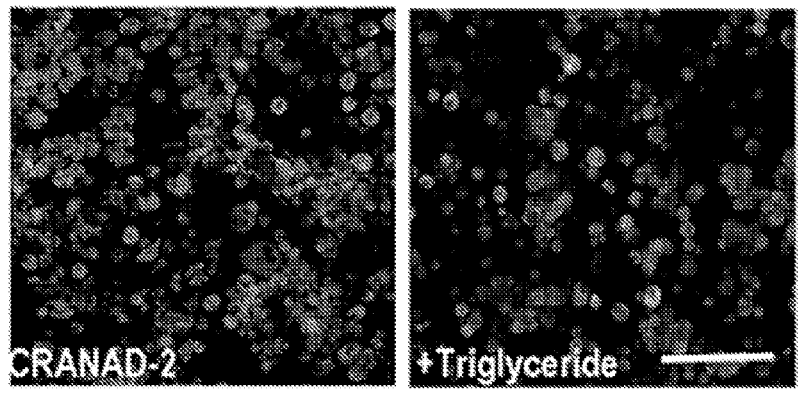
Figure 15C:
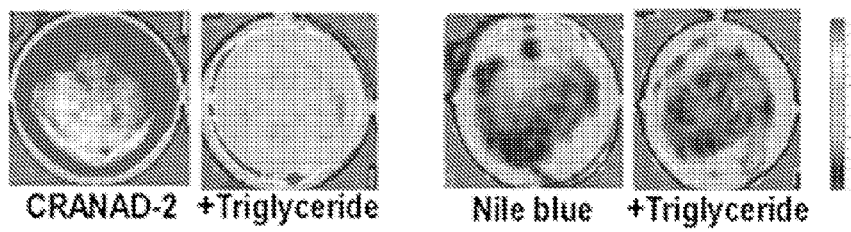
Figure 15D:
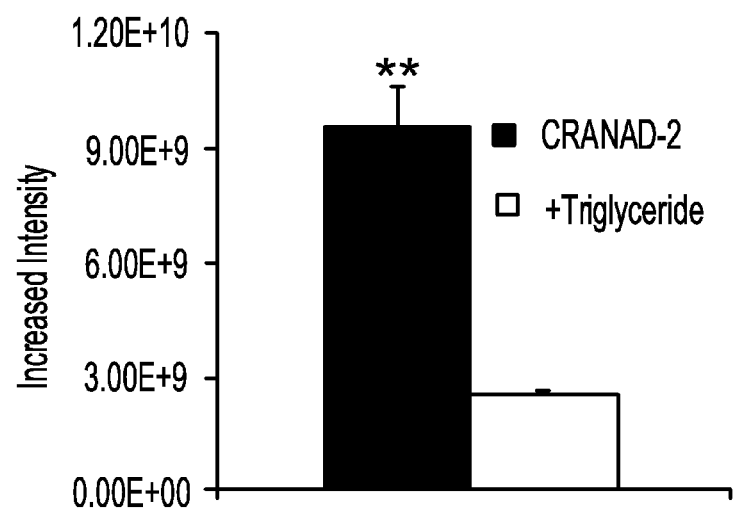
Figure 15E:
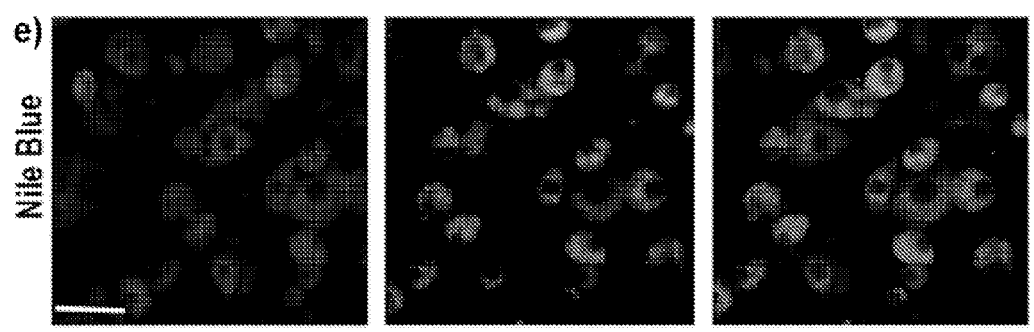

Through systemic comparison of gene expression in undifferentiated and differentiated 3T3-L1 cells, Sandoval et al found that CD36 was only present in differentiated cells but not in the preadipocytes (Sandoval et al. Arch. Biochem. Biophysics 477:363 (2008)). CD36 is highly expressed on the surface of adipose cells and endothelial cells of capillaries in adipose tissue, but not on other large vessels and brain capillaries (Coburn et al., J Mol Neurosci. 16(2-3): 117-121 (2001); Greenwalt et al., J Clin Invest. 96(3): 1382-8 (1995); Harmon and Abumrad, J Membr Biol. 133 (1):43-9 (1993); Zhou et al., FASEB J. 26(11):4733-42 (2012)). Recently, Bartelt et al reported that BAT regulates the metabolism of triglyceride through CD36 uptake (Williams and Fisher, Nat. Med. 17, 157 (2011); Bartelt, Nature medicine 17: 200-205 (2011)). Since CRANAD-2, like triglyceride, accumulates in oil droplets, it was hypothesized that triglyceride and the curcumin analogues described herein may share the same transporter/translocase. To test this hypothesis, both triglyceride and CRANAD-2 were added to the cell medium, and CRANAD-2 only was used as the control. A significant decrease in uptake was observed for the mixture of CRANAD-2 and triglyceride, evidenced by two-photon microscopy and quantitative imaging with IVIS imaging system (FIGS. 15B-D). However, no significant decrease in uptake was observed for Nile Blue (FIGS. 15C and 16C). These results indicated that triglyceride inhibited the uptake of CRANAD-2, probably due to binding competition for CD36. These data suggested that curcumin is a possible ligand for CD36.

Example 10

Uptake Mechanism Studies for CRANAD-29

The uptake of CRANAD-29 in 3T3-L1 cells before and after differentiation was compared. IVIS imaging of 3T3-L1 cells with CRANAD-29 was performed as follows. To a 6-well plate seeded with preadipocytes or differentiated adipocytes, a 10 µL solution of CRANAD-29 (250 µM in DMSO) was added. The plate was subjected to imaging using IVIS imaging system with Ex=640 nm, Em=700 nm before and after addition of CRANAD-29. For triglyceride competition and Hexarelin inhibition, the similar protocol for CRANAD-2 imaging was used. The final concentration of hexarelin was 12.5 µM, and the images were acquired at 3 hours after addition of CRANAD-29 and triglyceride/Hexarelin. Studies were performed in triplicate.

CRANAD-29 showed no apparent uptake in undifferentiated cells over the time course of the study (FIG. 17A, left panel), indicating no significant simple diffusion. Indeed, its uptake in differentiated cells was much slower than CRANAD-2 and reached its plateau around 90 minutes (FIG. 17A, middle panel), indicating the contribution from simple diffusion was minimized. It is known that facilitated diffusion can be significantly inhibited when the cells were fixed (Kaplan et al., J. Membr Biol. 20:181 (1975)). Indeed, the uptake of CRANAD-29 was reduced 70% when the differentiated 3T3-L1 cells were fixed with glutaraldehyde (FIG. 17A, right panel), suggesting CRANAD-29 was primarily transported via the facilitated transporting. Moreover, similar to CRANAD-2, the uptake of CRANAD-29 could be significantly reduced by triglyceride, indicating that CRANAD-29 transport was probably related to CD36 (FIGS. 17B-C). Additionally, the uptake of CRANAD-29 could be significantly inhibited by Hexarelin, a CD36 specific ligand (Demers et al., Biochem. J. 382:417 (2004); Baranova et al., J Biol Chem 285:8492 (2010)) (FIG. 17D). This data further indicated that the uptake of CRANAD-29 could be related to CD36-facilitated transport.

REFERENCES

1. Cannon B, Nedergaard J (2004) Brown adipose tissue: function and physiological significance. Physiological reviews 84: 277-359.

2. Richard D, Picard F (2011) Brown fat biology and thermogenesis. Frontiers in bioscience: a journal and virtual library 16: 1233-1260.
3. Ouellet V, Labbe S M, Blondin D P, Phoenix S, Guerin B, et al. (2012) Brown adipose tissue oxidative metabolism contributes to energy expenditure during acute cold exposure in humans. The Journal of clinical investigation 122: 545-552.
4. Cypess A M, Lehman S, Williams G, Tal I, Rodman D, et al. (2009) Identification and importance of brown adipose tissue in adult humans. The New England journal of medicine 360: 1509-1517.
5. Nedergaard J, Bengtsson T, Cannon B (2007) Unexpected evidence for active brown adipose tissue in adult humans. American journal of physiology Endocrinology and metabolism 293: E444-452.
6. Tran T T, Kahn C R (2010) Transplantation of adipose tissue and stem cells: role in metabolism and disease. Nature reviews Endocrinology 6: 195-213.
7. Tseng Y H, Kokkotou E, Schulz T J, Huang T L, Winnay J N, et al. (2008) New role of bone morphogenetic protein 7 in brown adipogenesis and energy expenditure. Nature 454: 1000-1004.
8. Zhang H, Schulz T J, Espinoza D O, Huang T L, Emanuelli B, et al. (2010) Cross talk between insulin and bone morphogenetic protein signaling systems in brown adipogenesis. Molecular and cellular biology 30: 4224-4233.
9. van Marken Lichtenbelt W D, Vanhommerig J W, Smulders N M, Drossaerts J M, Kemerink G J, et al. (2009) Cold-activated brown adipose tissue in healthy men. The New England journal of medicine 360: 1500-1508.
10. Yoneshiro T, Aita S, Matsushita M, Okamatsu-Ogura Y, Kameya T, et al. (2011) Age-related decrease in cold-activated brown adipose tissue and accumulation of body fat in healthy humans. Obesity 19: 1755-1760.
11. Boss O, Farmer S R (2012) Recruitment of brown adipose tissue as a therapy for obesity-associated diseases. Frontiers in endocrinology 3: 14.
12. Gunawardana S C, Piston D W (2012) Reversal of type 1 diabetes in mice by brown adipose tissue transplant. Diabetes 61: 674-682.
13. Kajimura S, Seale P, Tomaru T, Erdjument-Bromage H, Cooper M P, et al. (2008) Regulation of the brown and white fat gene programs through a PRDM16/CtBP transcriptional complex. Genes & development 22: 1397-1409.
14. Farmer S R (2008) Molecular determinants of brown adipocyte formation and function. Genes & development 22: 1269-1275.
15. Wilson-Fritch L, Nicoloro S, Chouinard M, Lazar M A, Chui P C, et al. (2004) Mitochondrial remodeling in adipose tissue associated with obesity and treatment with rosiglitazone. The Journal of clinical investigation 114: 1281-1289.
16. Qiang L, Wang L, Kon N, Zhao W, Lee S, et al. (2012) Brown remodeling of white adipose tissue by SirT1-dependent deacetylation of Ppargamma. Cell 150: 620-632.
17. Xu X, Ying Z, Cai M, Xu Z, Li Y, et al. (2011) Exercise ameliorates high-fat diet-induced metabolic and vascular dysfunction, and increases adipocyte progenitor cell population in brown adipose tissue. American journal of physiology Regulatory, integrative and comparative physiology 300: R1115-1125.
18. Bostrom P, Wu J, Jedrychowski M P, Korde A, Ye L, et al. (2012) A PGC1-alpha-dependent myokine that drives brown-fat-like development of white fat and thermogenesis. Nature 481: 463-468.
19. Himms-Hagen J, Melnyk A, Zingaretti M C, Ceresi E, Barbatelli G, et al. (2000) Multilocular fat cells in WAT of CL-316243-treated rats derive directly from white adipocytes. American journal of physiology Cell physiology 279: C670-681.
20. Schulz T J, Huang P, Huang T L, Xue R, McDougall L E, et al. (2013) Brown-fat paucity due to impaired BMP signalling induces compensatory browning of white fat. Nature 495: 379-383.
21. Mattson M P (2010) Perspective: Does brown fat protect against diseases of aging? Ageing research reviews 9: 69-76.
22. Pfannenberg C, Werner M K, Ripkens S, Stef I, Deckert A, et al. (2010) Impact of age on the relationships of brown adipose tissue with sex and adiposity in humans. Diabetes 59: 1789-1793.
23. Nagajyothi F, Desruisseaux M S, Machado F S, Upadhya R, Zhao D, et al. (2012) Response of adipose tissue to early infection with *Trypanosoma cruzi* (Brazil strain). The Journal of infectious diseases 205: 830-840.
24. Herrero L, Shapiro H, Nayer A, Lee J, Shoelson S E (2010) Inflammation and adipose tissue macrophages in lipodystrophic mice. Proceedings of the National Academy of Sciences of the United States of America 107: 240-245.
25. Basu S (2008) Functional imaging of brown adipose tissue with PET: can this provide new insights into the pathophysiology of obesity and thereby direct antiobesity strategies? Nuclear medicine communications 29: 931-933.
26. Bartell A, Bruns O T, Reimer R, Hohenberg H, Ittrich H, et al. (2011) Brown adipose tissue activity controls triglyceride clearance. Nature medicine 17: 200-205
27. Aleo M D, Lundeen G R, Blackwell D K, Smith W M, Coleman G L, et al. (2003) Mechanism and implications of brown adipose tissue proliferation in rats and monkeys treated with the thiazolidinedione darglitazone, a potent peroxisome proliferator-activated receptor-gamma agonist. The Journal of pharmacology and experimental therapeutics 305: 1173-1182.
28. Wu C, Cheng W, Xing H, Dang Y, Li F, et al. (2011) Brown adipose tissue can be activated or inhibited within an hour before 18F-FDG injection: a preliminary study with microPET. Journal of biomedicine & biotechnology 2011: 159834.
29. Tatsumi M, Engles J M, Ishimori T, Nicely O, Cohade C, et al. (2004) Intense (18)F-FDG uptake in brown fat can be reduced pharmacologically. Journal of nuclear medicine: official publication, Society of Nuclear Medicine 45: 1189-1193
30. Zhang X, Kuo C, Moore A, Ran C (2013) In Vivo Optical Imaging of Interscapular Brown Adipose Tissue with 18F-FDG via Cerenkov Luminescence Imaging. Plos One: In press.
31. Madar I, Isoda T, Finley P, Angle J, Wahl R (2011) 18F-fluorobenzyl triphenyl phosphonium: a noninvasive sensor of brown adipose tissue thermogenesis. Journal of nuclear medicine: official publication, Society of Nuclear Medicine 52: 808-814.
32. Hu H H, Smith D L, Jr., Nayak K S, Goran M I, Nagy T R (2010) Identification of brown adipose tissue in mice with fat-water IDEAL-MRI. Journal of magnetic resonance imaging: JMRI 31: 1195-1202.

33. Chen Y I, Cypess A M, Sass C A, Brownell A L, Jokivarsi K T, et al. (2012) Anatomical and Functional Assessment of Brown Adipose Tissue by Magnetic Resonance Imaging. Obesity 20: 1519-1526.
34. Khanna A, Branca R T (2012) Detecting brown adipose tissue activity with BOLD MRI in mice. Magnetic resonance in medicine: official journal of the Society of Magnetic Resonance in Medicine/Society of Magnetic Resonance in Medicine 68: 1285-1290.
35. Weissleder R (2001) A clearer vision for in vivo imaging. Nature biotechnology 19: 316-317.
36. Haucke G, Czerney P, Ilge H-D, Steen D, Hartmann H (1990) The effect of internal rotation on absorption and fluorescence of dye molecules. Journal of Molecular Structure: 411-416.
37. Ran C, Xu X, Raymond S B, Ferrara B J, Neal K, et al. (2009) Design, synthesis, and testing of difluoroboron-derivatized curcumins as near-infrared probes for in vivo detection of amyloid-beta deposits. Journal of the American Chemical Society 131: 15257-15261.
38. Ran C, Moore A (2011) Spectral Unmixing Imaging of Wavelength-Responsive Fluorescent Probes: An Application for the Real-Time Report of Amyloid Beta Species in Alzheimer's Disease. Molecular imaging and biology: MIB: the official publication of the Academy of Molecular Imaging.
39. Jamal Z, Saggerson E D (1988) Changes in brown-adipose-tissue mitochondrial processes in streptozotocin-diabetes. The Biochemical journal 252: 293-296.
40. Seydoux J, Chinet A, Schneider-Picard G, Bas S, Imesch E, et al. (1983) Brown adipose tissue metabolism in streptozotocin-diabetic rats. Endocrinology 113: 604-610.
41. Burcelin R, Kande J, Ricquier D, Girard J (1993) Changes in uncoupling protein and GLUT4 glucose transporter expressions in interscapular brown adipose tissue of diabetic rats: relative roles of hyperglycaemia and hypoinsulinaemia. The Biochemical journal 291 (Pt 1): 109-113.
42. Ocloo A, Shabalina I G, Nedergaard J, Brand M D (2007) Cold-induced alterations of phospholipid fatty acyl composition in brown adipose tissue mitochondria are independent of uncoupling protein-1. American journal of physiology Regulatory, integrative and comparative physiology 293: R1086-1093.
43. Kim H, Pennisi P A, Gavrilova O, Pack S, Jou W, et al. (2006) Effect of adipocyte beta3-adrenergic receptor activation on the type 2 diabetic MKR mice. American journal of physiology Endocrinology and metabolism 290: E1227-1236.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of imaging brown adipose tissue (BAT) in a mammal, the method comprising:
administering to the mammal a BAT imaging agent of Formula I:

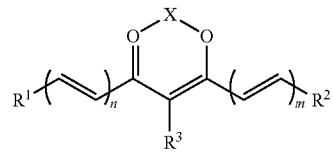

or a pharmaceutically acceptable salt thereof, wherein:
X is —$BR^4R^5$ or absent;
$R^1$ is a substituted or unsubstituted aryl or a substituted or unsubstituted heteroaryl;
$R^2$ is a substituted or unsubstituted aryl or a substituted or unsubstituted heteroaryl;
$R^3$ is H or a $(C_1-C_6)$alkyl;
$R^4$ and $R^5$ are independently selected from the group consisting of H, halo, and $OR^6$;
$R^6$ is H or a $(C_1-C_6)$alkyl;
n and m are independently 1 or 2; and
detecting the imaging agent in the mammal,
thereby imaging BAT in the mammal.

2. A method of detecting brown adipose tissue (BAT) levels or activity in a mammal, the method comprising:
administering to the mammal a BAT imaging agent of Formula I:

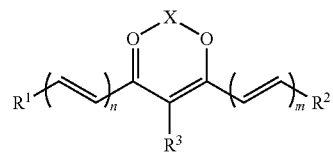

or a pharmaceutically acceptable salt thereof, wherein:
X is —$BR^4R^5$ or absent;
$R^1$ is a substituted or unsubstituted aryl or a substituted or unsubstituted heteroaryl;
$R^2$ is a substituted or unsubstituted aryl or a substituted or unsubstituted heteroaryl;
$R^3$ is H or a $(C_1-C_6)$alkyl;
$R^4$ and $R^5$ are independently selected from the group consisting of H, halo, and $OR^6$;
$R^6$ is H or a $(C_1-C_6)$alkyl;
n and m are independently 1 or 2; and
detecting the imaging agent in the mammal, to obtain an image of BAT in the mammal; and
processing the image to provide a measure of BAT levels or activity in the mammal.

3. The method of claim 1, wherein detecting the imaging agent comprises detecting fluorescence emission from the imaging agent; detecting gamma rays; detecting nuclear magnetic resonance (NMR); or detecting ultrasonic emissions.

4. The method of claim 1, wherein the BAT imaging agent is selected from the group consisting of CRANAD-2, CRANAD-3, CRANAD-29, and CRANAD-43.

5. The method of claim 1, wherein detecting the imaging agent comprises:
setting a region of interest (ROI); and
obtaining an image of the region of interest in the mammal.

6. The method of claim 5, further comprising processing the image to provide a measure of BAT levels or activity in the mammal.

7. The method of claim 2, comprising one or both of:
administering CRANAD-2 to the mammal, and processing the image to provide a measure of BAT activity, and/or
administering CRANAD-29 to the mammal, and processing the image to provide a measure of BAT levels.

8. The method of claim 5, wherein the ROI covers one or more of the cervical, supraclavicular, and superior mediastinal areas of the mammal.

9. The method of claim 1, comprising:
obtaining an image by detecting fluorescence emission from the imaging agent, or detecting ultrasonic emissions; and
processing the image to provide information regarding BAT levels or activity in the mammal.

10. The method of claim 9, comprising:
scanning the ROI with an infrared camera to obtain an infrared thermographic image of the region of interest in the mammal;
processing the image to provide a measure of temperature information;
wherein the temperature information provides information regarding BAT levels or activity in the mammal.

11. The method of claim 1, wherein the imaging agent comprises a positron-emitting radionuclide, and the method comprises:
obtaining an image by detecting gamma radiation from the BAT imaging agent; and
processing the image to provide information regarding BAT levels or activity in the mammal.

12. The method of claim 1, wherein the imaging agent comprises $^{13}C$, $^{17}O$, or $^{19}F$ atom, and the method comprises:
obtaining an image by detecting BAT using an imaging modality suitable for detecting the spin of those labeled agents; and
processing the image to provide information regarding BAT levels or activity in the mammal.

13. The method claim 2, further comprising comparing the measure of BAT levels or activity to a predetermined value, the predetermined value being a measure of BAT levels or activity in either the same subject, or a measure that represents BAT levels or activity in one or more control subjects.

14. The method of claim 12, wherein the predetermined value is a measure of BAT levels or activity in the ROI of the same subject before or after administration of a test compound, wherein the comparison indicates an effect of the test compound on BAT levels or activity.

15. A method of detecting an effect of a test compound on brown adipose tissue (BAT) levels or activity in a mammal, the method comprising:
administering a test compound to the mammal;
administering to the mammal a BAT imaging agent of Formula I:

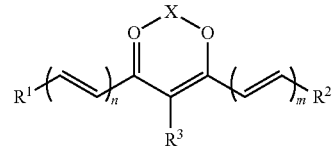

or a pharmaceutically acceptable salt thereof, wherein:
X is $-BR^4R^5$ or absent;
$R^1$ is a substituted or unsubstituted aryl or a substituted or unsubstituted heteroaryl;
$R^2$ is a substituted or unsubstituted aryl or a substituted or unsubstituted heteroaryl;
$R^3$ is H or a $(C_1-C_6)$alkyl;
$R^4$ and $R^5$ are independently selected from the group consisting of H, halo, and $OR^6$;
$R^6$ is H or a $(C_1-C_6)$alkyl;
n and m are independently 1 or 2; and
detecting the imaging agent in the mammal, to obtain an image of BAT in the mammal;
processing the image to provide a measure of BAT levels or activity in the mammal after administration of the test compound;
comparing the measure of BAT levels or activity in the mammal after administration of the test compound to a reference measure of BAT levels or activity, to detect an increase, decrease, or no change in BAT levels or activity in the mammal;
thereby determining the effect of the test compound on BAT levels or activity in the mammal.

16. The method of claim 15, further comprising selecting a test compound that increases BAT levels or activity in the mammal as a candidate compound for the treatment of obesity or a metabolic disorder.

17. The method of claim 15, wherein detecting the imaging agent in the mammal comprises setting a region of interest (ROI); and obtaining an image of the region of interest in the mammal.

18. The method of claim 17, wherein the ROI includes an area comprising white adipose tissue (WAT) in the subject, and an increase in BAT levels or activity in the ROI indicates that the test compound induces or enhances browning of white fat.

19. The method of claim 2, further comprising selecting, rejecting, or stratifying the subject for participation in a clinical trial based on BAT levels or activity in the subject.

20. The method of claim 2, further comprising comparing the measure of BAT levels or activity in the mammal to a subsequent measure of BAT levels or activity obtained after administration of a test compound, to detect an increase, decrease, or no change in BAT levels or activity in the mammal;
thereby determining the effect of the test compound on BAT levels or activity in the mammal.

* * * * *

UNITED STATES PATENT AND TRADEMARK OFFICE
CERTIFICATE OF CORRECTION

PATENT NO. : 9,757,477 B2
APPLICATION NO. : 14/916779
DATED : September 12, 2017
INVENTOR(S) : Anna-Liisa Brownell, Chongzhao Ran and Anna Moore Page 1 of 1

It is certified that error appears in the above-identified patent and that said Letters Patent is hereby corrected as shown below:

In the Claims

In Column 31, Line 41, in Claim 13, after "method" insert -- of --

Signed and Sealed this
Fourth Day of February, 2020

Andrei Iancu
*Director of the United States Patent and Trademark Office*